United States Patent
Juhl et al.

(10) Patent No.: US 10,538,525 B2
(45) Date of Patent: Jan. 21, 2020

(54) 1,5-DIHYDRO-4H-PYRAZOLO [3,4-D]PYRIMIDIN-4-ONES AND 1,5-DIHYDRO-4H-PYRAZOLO [4,3-C]PYRIDIN-4-ONES AS PDE1 INHIBITORS

(71) Applicant: H. Lundbeck A/S, Valby (DK)

(72) Inventors: Karsten Juhl, Greve (DK); Mikkel Jessing, Frederiksberg (DK); Morten Langgård, Glostrup (DK); Paulo Jorge Vieira Vital, København V (DK); Mauro Marigo, Skovlunde (DK); Jan Kehler, Lyngby (DK); Lars Kyhn Rasmussen, Vanløse (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/051,612

(22) Filed: Aug. 1, 2018

(65) Prior Publication Data

US 2019/0194204 A1    Jun. 27, 2019

Related U.S. Application Data

(63) Continuation of application No. 15/481,083, filed on Apr. 6, 2017, now abandoned.

(30) Foreign Application Priority Data

Apr. 12, 2016   (DK) .................................. 2016 00221

(51) Int. Cl.
| | | |
|---|---|---|
| C07D 487/04 | (2006.01) | |
| C07D 471/04 | (2006.01) | |
| A61K 31/437 | (2006.01) | |
| A61K 31/519 | (2006.01) | |

(52) U.S. Cl.
CPC .......... *C07D 487/04* (2013.01); *A61K 31/437* (2013.01); *A61K 31/519* (2013.01); *C07D 471/04* (2013.01)

(58) Field of Classification Search
None
See application file for complete search history.

(56) References Cited

U.S. PATENT DOCUMENTS

| | | |
|---|---|---|
| 7,872,124 B2 | 1/2011 | Feng et al. |
| 10,011,606 B2 | 7/2018 | Kehler et al. |
| 10,150,771 B2 | 12/2018 | Kehler et al. |
| 2006/0135767 A1 | 6/2006 | Feng et al. |
| 2008/0194592 A1 | 8/2008 | Mates et al. |
| 2009/0143391 A1 | 6/2009 | Hofgen et al. |
| 2010/0190771 A1 | 7/2010 | Claffey et al. |
| 2011/0281832 A1 | 11/2011 | Li et al. |
| 2016/0083391 A1 | 3/2016 | Burdi et al. |
| 2016/0083400 A1 | 3/2016 | Burdi et al. |
| 2016/0311831 A1 | 10/2016 | Kehler et al. |
| 2016/0318939 A1 | 11/2016 | Kehler et al. |
| 2017/0291901 A1 | 10/2017 | Juhl et al. |
| 2017/0291903 A1 | 10/2017 | Kehler et al. |
| 2017/0298072 A1 | 10/2017 | Kehler et al. |
| 2019/0062335 A1 | 2/2019 | Kehler et al. |

FOREIGN PATENT DOCUMENTS

| | | |
|---|---|---|
| EP | 2305262 | 4/2011 |
| GB | 973361 | 10/1964 |
| JP | 2015-052588 | 2/2016 |
| JP | 2016-011511 | 2/2016 |
| WO | WO 2004/018474 | 3/2004 |
| WO | WO 2004/026876 | 4/2004 |
| WO | WO 2004/099211 | 11/2004 |
| WO | WO 2008/070095 | 6/2008 |
| WO | WO 2008/139293 | 11/2008 |
| WO | WO 2009/121919 A1 | 10/2009 |
| WO | WO 2010/026214 A1 | 3/2010 |
| WO | WO 2010/065152 | 6/2010 |
| WO | WO 2010/084438 | 7/2010 |
| WO | WO 2011/153136 | 12/2011 |
| WO | WO 2012/040048 | 3/2012 |
| WO | WO 2012/040230 | 3/2012 |
| WO | WO 2012/065612 A1 | 5/2012 |
| WO | WO 2012/171016 | 12/2012 |
| WO | WO 2013/053690 | 4/2013 |
| WO | WO 2013/110768 | 8/2013 |
| WO | WO 2013/192225 A1 | 12/2013 |
| WO | WO 2013/192229 A1 | 12/2013 |
| WO | WO 2014/151409 | 9/2014 |
| WO | WO 2016/042775 | 3/2016 |
| WO | WO 2016/055618 | 4/2016 |
| WO | WO 2016/147659 | 9/2016 |
| WO | WO 2016/170064 A1 | 10/2016 |
| WO | WO 2016/174188 | 11/2016 |
| WO | WO 2017/139186 A1 | 8/2017 |
| WO | WO 2018/073251 A1 | 4/2018 |
| WO | WO 2018/078038 A1 | 5/2018 |
| WO | WO 2018/078042 A1 | 5/2018 |

OTHER PUBLICATIONS

International Search Report and Written Opinion dated Dec. 2, 2015 for Application No. PCT/EP2015/073417.

(Continued)

*Primary Examiner* — Alicia L Otton
(74) *Attorney, Agent, or Firm* — Wolf, Greenfield & Sacks, P.C.

(57) ABSTRACT

The present invention provides 1,5-dihydro-4H-pyrazolo[3, 4-d]pyrimidin-4-ones and 1,5-dihydro-4H-pyrazolo[4,3-c] pyridin-4-ones of formula (I) as PDE1 inhibitors and their use as a medicament, in particular for the treatment of neurodegenerative disorders and psychiatric disorders.

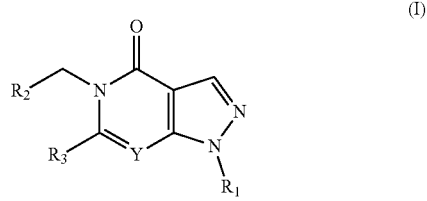

(I)

15 Claims, No Drawings

(56) References Cited

OTHER PUBLICATIONS

International Search Report and Written Opinion dated Jun. 2, 2016 for Application No. PCT/EP2016/058910.
International Search Report and Written Opinion dated Jul. 21, 2016 for Application No. PCT/EP2016/059583.
International Search Report and Written Opinion dated May 15, 2017 for Application No. PCT/EP2017/058332.
International Search Report and Written Opinion dated Dec. 11, 2017 for Application No. PCT/EP2017/076481.
International Search Report and Written Opinion dated Feb. 2, 2018 for Application No. PCT/EP2017/077497.
International Search Report and Written Opinion dated Feb. 7, 2018 for Application No. PCT/EP2017/077503.
[No Author Listed] FDA mulls drug to slow late-stage Alzheimer's. CNN Health. Sep. 24, 2003; http://www.cnn.com/2003/HEALTH/conditions/09/24/alzheimers.drug.ap/index.html [obtained Oct. 9, 2010].
Berge et al., Pharmaceutical Salts. J Pharm Sci. Jan. 1977;66(1):1-19.
Bernard et al., Transcriptional architecture of the primate neocortex. Neuron. Mar. 22, 2012;73(6):1083-99. doi: 10.1016/j.neuron.2012.03.002.
Blokland et al., PDE inhibition and cognition enhancement. Expert Opin Ther Pat. Apr. 2012;22(4):349-54. doi: 10.1517/13543776.2012.674514.
CAS Registry No. 1296334-75-2 (May 18, 2011).
Chan et al., PD El Isozymes, Key Regulators of Pathological Vascular Remodeling. Curr. Opin. Pharmacol. 2011; 11( 6) :720-724.
Damasio et al., Alzheimer's Disease and Related Dementias. Cecil Textbook of Medicine. 20th edition. 1996;2:1992-1996.
Finlander et al., Phosphorus Pentoxide in Organic Synthesis V. Phosphorus Pentoxide and Amine Hydrochlorides as Reagents in the Synthesis of 1,5-dihydro-1-methyl-4H-pyrazolo[3,4-dlpyrimidin-4-ones. Chemica Scripta. 1983;22( 4):171-176 (Chemical Abstracts Only).
Francis et al., Mammalian cyclic nucleotide phosphodiesterases: molecular mechanisms and physiological functions. Physiol Rev. Apr. 2011;91(2):651-90. doi: 10.1152/physrev.00030.2010.
Medina, (2011) Therapeutic Utility of Phosphodiesterase Type I Inhibitors in Neurological Conditions. Front Neurosci. 2011; 5:21. Published online Feb. 18, 2011. Prepublished online Jan. 19, 2011. doi: 10.3389/fnins.2011.00021.

1,5-DIHYDRO-4H-PYRAZOLO [3,4-D]PYRIMIDIN-4-ONES AND 1,5-DIHYDRO-4H-PYRAZOLO [4,3-C]PYRIDIN-4-ONES AS PDE1 INHIBITORS

CROSS-REFERENCE TO RELATED APPLICATIONS

This application is a Continuation application of U.S. application Ser. No. 15/481,083 (filed: Apr. 6, 2017), which claims priority to Danish Patent Application No. PA201600221 (filed: Apr. 12, 2016), which applications are herein incorporated by reference in their entirety.

FIELD OF THE INVENTION

The present invention provides compounds that are PDE1 enzyme inhibitors and their use as a medicament, in particular for the treatment of neurodegenerative disorders and psychiatric disorders.

The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signaling. The catalytic activities of PDEs provide for breakdown of cNs over a spectrum of cN-concentrations in all cells, and their varied regulatory mechanisms provide for integration and crosstalk with myriad signaling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol. Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain that contains two $Ca^{2+}$/CaM binding domains and two phosphorylation sites differentiate their corresponding proteins and modulate their biochemical functions. PDE1 is a dual substrate PDE and the PDE1C-subtype has equal activity towards cAMP and cGMP (Km≈1-3 µM), whereas the subtypes PDE1A and PDE1B have a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signaling pathways, preferably in the nervous system and PDE1 inhibitors can enhance the levels of the second messengers cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 (February), 21) have suggested the potential for the therapeutic use of PDE1 inhibitors in neurological disorders, like e.g. Alzheimer's, Parkinson's and Huntington's Diseases and in psychiatric disorders like e.g. Attention Deficit hyperactivity Disorder (ADHD), restless leg syndrome, depression, narcolepsy, cognitive impairment and cognitive impairment associated with schizophrenia (CIAS). There have also been patent applications claiming that PDE1 inhibitors are useful in diseases that may be alleviated by the enhancement of progesterone-signaling such as female sexual dysfunction (e.g. WO 2008/070095).

WO 2008/139293 and WO 2010/084438 (Pfizer Inc.) and WO 2004/099211 (Bayer AG) disclose 1,5-dihydro-4H-pyrazolo[3,4-d]pyrimidin-4-ones as PDE9 inhibitors.

The compounds of the invention may offer alternatives to current marketed treatments for neurodegenerative and/or psychiatric disorders, treatments which are not efficacious in all patients. Hence, there remains a need for alternative methods of treatment.

SUMMARY OF THE INVENTION

PDE1 enzymes are expressed in the Central Nervous System (CNS), making this gene family an attractive source of new targets for the treatment of psychiatric and neurodegenerative disorders.

The objective of the present invention is to provide compounds that are PDE1 inhibitors, and as such are useful to treat neurodegenerative disorders and psychiatric disorders. Preferably, said compounds are at least a ten-fold stronger as PDE1 inhibitors than as PDE9 inhibitors in order to prevent potentially unwanted effects associated with PDE9 inhibition.

Accordingly, the present invention relates to compounds of formula (I)

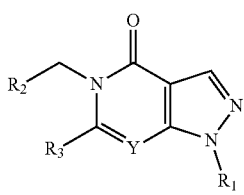

(I)

wherein
Y is N or CH;
$R_1$ is selected from the group consisting of linear or branched $C_2$-$C_8$ alkyl, saturated monocyclic $C_3$-$C_8$ cycloalkyl, oxetanyl, tetrahydrofuranyl and tetrahydropyranyl; all of which can be substituted one or more times with one or more substituents selected from the group consisting of methyl, fluorine, hydroxy, cyano or methoxy;
$R_2$ is selected from the group consisting of, linear or branched $C_1$-$C_8$ alkyl, phenyl, benzo[1,3]dioxole and saturated monocyclic $C_3$-$C_8$ cycloalkyl; or
$R_2$ is phenyl substituted one or more times with one or more substituents selected from the group consisting of halogen, $C_1$-$C_3$ alkyl and methoxy; or
$R_2$ is pyridinyl substituted with a substituent selected from the group consisting of halogen, $C_1$-$C_3$ alkyl, $C_1$-$C_3$ alkoxy, $C_1$-$C_3$ fluoroalkoxy, $C_3$-$C_4$ cycloalkoxy and $C_4$-$C_5$ methylcycloalkoxy; or
$R_2$ is selected from the group consisting of 5-membered heteroaryls substituted with $C_1$-$C_3$ alkyl;
$R_3$ is selected from the group consisting of linear or branched $C_1$-$C_3$ alkyl and saturated monocyclic $C_3$-$C_8$ cycloalkyl; which can each be optionally substituted with a substituent selected from halogen, $C_1$-$C_3$ alkoxy, phenyl, dialkylamine and oxetane; and tautomers and pharmaceutically acceptable salts thereof.

Reference to Compound (I) includes the free base of Compound (I), pharmaceutically acceptable salts of Compound I, such as acid addition salts of Compound (I), racemic mixtures of Compound (I), or the corresponding enantiomer and/or optical isomer of Compound I, and polymorphic and amorphic forms of Compound (I) as well as tautomeric forms of Compound (I). Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

In one embodiment, the invention relates to a compound according to formula (I) for use in therapy.

In one embodiment, the invention relates to a compound according to formula (I), for use in the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a pharmaceutical composition comprising a compound according to formula (I), and one or more pharmaceutically acceptable carrier or excipient.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) to a patient in need thereof.

In one embodiment, the invention relates to the use of a compound according to formula (I), for the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome.

Definitions

Pde1 Enzymes:
The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.

PDE1 Inhibitors and PDE9 Inhibitors:
In the context of the present invention a compound is considered to be a PDE1 inhibitor if the amount required to reach the $IC_{50}$ level of any of the three PDE1 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less. In preferred embodiments the required amount of PDE1 inhibitor required to reach the $IC_{50}$ level of PDE1B is 400 nM or less, such as 300 nM or less, 200 nM or less, 100 nM or less, or even 80 nM or less, such as 50 nM or less, for example 25 nM or less.

In a preferred embodiment the compounds of the present invention are at least a ten-fold stronger as PDE1 inhibitors as PDE9 inhibitors, i.e. the amount of the compound required to reach the $IC_{50}$ level of one or more of the three PDE1 isoforms is at least a ten-fold less than the amount of the same compound required to reach the $IC_{50}$ level of the PDE9 enzyme.

Substituents:

In the present context, "optionally substituted" means that the indicated moiety may or may not be substituted, and when substituted is mono-, di-, or tri-substituted. It is understood that where no substituents are indicated for an "optionally substituted" moiety, then the position is held by a hydrogen atom.

As used in the context of the present invention, the terms "halo" and "halogen" are used interchangeably and refer to fluorine, chlorine, bromine or iodine.

A given range may interchangeably be indicated with "-" (dash) or "to", e.g. the term "$C_1$-$C_3$ alkyl" is equivalent to "$C_1$ to $C_3$ alkyl".

The terms "$C_1$-$C_3$ alkyl", "$C_1$-$C_4$ alkyl", "$C_1$-$C_5$ alkyl", "$C_1$-$C_6$ alkyl", "$C_1$-$C_7$ alkyl" and "$C_1$-$C_8$ alkyl" refer to a linear (i.e. unbranched) or branched saturated hydrocarbon having from one up to eight carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, n-hexyl, n-heptyl and n-octyl.

The term saturated monocyclic $C_3$-$C_8$ cycloalkyl refers to cyclopropyl, cyclobutyl, cyclopentyl, cyclohexyl, cycloheptyl and cyclooctyl.

The term "heteroaryl" refers to a 5 or 6 membered aromatic monocyclic ring containing 1 to 5 carbon atoms and one or more heteroatoms selected from oxygen, nitrogen and sulfur.

The term "dialkylamine" refers to an amino group substituted with two $C_1$-$C_3$ alkyl groups.

The term "$C_3$-$C_4$ alkoxy" refers to a moiety of the formula —OR', wherein R' indicates $C_1$-$C_3$ alkyl as defined above. $C_1$-$C_3$ fluoroalkoxy refers to a $C_1$-$C_3$ alkoxy substituted with one or more fluorine.

The term "$C_3$-$C_4$ cycloalkoxy" refers to a moiety of the formula —OR', wherein R' is a saturated monocyclic $C_3$-$C_4$ cycloalkyl group. The term "$C_4$-$C_5$ methylcycloalkoxy" is refers to a methyl group substituted with a $C_4$-$C_5$ cycloalkoxy group.

Isomeric and Tautomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

Furthermore, some of the compounds of the present invention may exist in different tautomeric forms and it is intended that any tautomeric forms that the compounds are able to form are included within the scope of the present invention.

Pharmaceutically Acceptable Salts:

The compounds of this invention are generally utilized as the free substance or as a pharmaceutically acceptable salt thereof. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount:

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting or delaying progress of the clinical manifestation of the disease, or curing the disease. The patient to be treated is preferably a mammal, in particular a human being.

Administration Routes

The pharmaceutical compositions may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a process for making a pharmaceutical composition comprising a compound of formula (I). The pharmaceutical compositions according to the invention may be formulated with pharmaceutically acceptable excipients in accordance with conventional techniques such as those disclosed in Remington, The Science and Practice of Pharmacy, $22^{th}$ edition (2012), Edited by Allen, Loyd V., Jr.

In an embodiment, the present invention relates to a pharmaceutical composition comprising a compound of formula (I), such as one of the compounds disclosed in the Experimental Section herein.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose.

If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

DETAILED DESCRIPTION OF THE INVENTION

The present inventors have identified compounds that are PDE1 inhibitors, and as such are useful to treat neurodegenerative and psychiatric disorders. Surprisingly, the compounds of the invention are significantly stronger as PDE1 inhibitors compared to being PDE9 inhibitors, The invention thus provides a compound of formula (I) or a pharmaceutically acceptable salt thereof, as well as a pharmaceutical composition containing such a compound, for use in the treatment of another brain disease which could be a neurodegenerative disorder or a psychiatric disorder. In a preferred embodiment, the neurodegenerative disorder is selected from the group consisting of Alzheimer's Disease, Parkinson's Disease and Huntington's Disease. In another preferred embodiment, the psychiatric disorder is selected from the group consisting of Attention Deficit hyperactivity Disorder (ADHD), depression, anxiety, narcolepsy, cognitive impairment and cognitive impairment associated with schizophrenia (CIAS). Other brain disorders could be e.g. restless leg syndrome.

The present invention provides a method of treating a mammal, including a human, suffering from a neurodegenerative disorder selected from the group consisting of Alzheimer's Disease, Parkinson's Disease and Huntington's Disease, which method comprises administering to the subject a therapeutically effective amount of a compound of formula (I).

This invention further provides a method of treating a neurodegenerative disorder in a mammal, including a human, which method comprises administering to said mammal an amount of a compound of formula (I) effective in inhibiting PDE1.

This invention also provides a method of treating a subject suffering from a psychiatric disorder, which method comprises administering to the subject a therapeutically effective amount of a compound of formula (I). Examples of psychiatric disorders that can be treated according to the present invention include Attention Deficit Hyperactivity Disorder (ADHD), depression, narcolepsy, cognitive impairment and cognitive impairment associated with schizophrenia (CIAS).

This invention also provides a method of treating a subject suffering from a brain disorder such as restless leg syndrome.

Embodiments of the Invention

In the following, embodiments of the invention are disclosed. The first embodiment is denoted E1, the second embodiment is denoted E2 and so forth In a first embodiment, E1, the present invention relates to compounds of formula (I).

E1. A compound of formula (I)

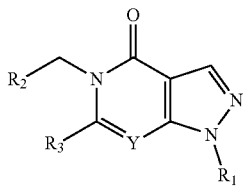

wherein
Y is N or CH;
R$_1$ is selected from the group consisting of linear or branched C$_2$-C$_8$ alkyl, saturated monocyclic C$_3$-C$_8$ cycloalkyl, oxetanyl, tetrahydrofuranyl and tetrahydropyranyl; all of which can be substituted one or more times with one or more substituents selected from the group consisting of methyl, fluorine, hydroxy, cyano or methoxy;
R$_2$ is selected from the group consisting of, linear or branched C$_1$-C$_8$ alkyl, phenyl, benzo[1,3]dioxole and saturated monocyclic C$_3$-C$_8$ cycloalkyl; or
R$_2$ is phenyl substituted one or more times with one or more substituents selected from the group consisting of halogen, C$_1$-C$_3$ alkyl and methoxy; or
R$_2$ is pyridyl substituted with a substituent selected from the group consisting of halogen, C$_1$-C$_3$ alkyl, C$_1$-C$_3$ alkoxy, C$_1$-C$_3$ fluoroalkoxy, C$_3$-C$_4$ cycloalkoxy and C$_4$-C$_5$ methylcycloalkoxy; or
R$_2$ is selected from the group consisting of 5-membered heteroaryls substituted with C$_1$-C$_3$ alkyl;
R$_3$ is selected from the group consisting of linear or branched C$_1$-C$_3$ alkyl and saturated monocyclic C$_3$-C$_8$ cycloalkyl; which can each be optionally substituted with a substituent selected from halogen, C$_1$-C$_3$ alkoxy, phenyl, dialkylamine and oxetane;
and tautomers and pharmaceutically acceptable salts thereof.

E2. The compound of embodiment 1, wherein Y is N.
E3. The compound of embodiment 1, wherein Y is CH.
E4. The compound of any one of embodiments 1-3, wherein R$_1$ is a linear or branched C$_2$-C$_8$ alkyl or a saturated monocyclic C$_3$-C$_8$ cycloalkyl such as cyclopropyl.
E5. The compound of embodiment 4, wherein said linear or branched C$_2$-C$_8$ alkyl or saturated monocyclic C$_3$-C$_8$ cycloalkyl is substituted one or more times with one or more substituents selected from the group consisting of methyl, fluorine, hydroxy, cyano or methoxy.
E6. The compound of any one of embodiments 1-3, wherein R$_1$ is selected from oxetanyl, tetrahydrofuranyl and tetrathydropyranyl.
E7. The compound of any one of embodiments 1-6, wherein R$_2$ is phenyl.
E8. The compound of embodiment 7, wherein said phenyl is substituted with one or more substituents selected from methyl, methoxy, fluorine or chlorine.
E9. The compound of any one of embodiments 1-6, wherein R$_2$ is pyridyl substituted with a substituent selected from methyl, methoxy, fluorine or chlorine.
E10. The compound of any one of embodiments 1-6, wherein R$_2$ is a saturated monocyclic C$_3$-C$_8$ cycloalkyl such as cyclohexyl.
E11. The compound of any one of embodiments 1-10, wherein R$_3$ is C$_{1-3}$ alkyl such as methyl.
E12. The compound of any one of embodiments 1-10, wherein R$_3$ is methyl substituted with a phenyl.
E13. The compound of any one of embodiments 1-10, wherein R$_3$ is methyl substituted with a methoxy or oxetane
E14. The compound of embodiment 1, wherein
Y is N or CH;
R$_1$ is selected from the group consisting of linear or branched C$_2$-C$_8$ alkyl, saturated monocyclic C$_3$-C$_8$ cycloalkyl, oxetanyl, tetrahydrofuranyl, and tetrathydropyranyl; all of which can be substituted one or more times with one or more substituents selected from the group consisting of methyl, fluorine, hydroxy, cyano or methoxy;
R$_2$ is selected from the group consisting of phenyl, benzo [1,3]dioxole, and saturated monocyclic C$_3$-C$_8$ cycloalkyl; or
R$_2$ is phenyl substituted one or more times with one or more substituents selected from the group consisting of halogen, C$_1$-C$_3$ alkyl and C$_1$-C$_3$ alkoxy; or
R$_2$ is pyridine substituted with a substituent selected from the group consisting of halogen, C$_1$-C$_3$ alkyl and C$_1$-C$_3$ alkoxy, C$_1$-C$_3$ fluoroalkoxy, C$_3$-C$_4$ cycloalkoxy and C$_4$-C$_5$ methylcycloalkoxy;
R$_3$ is C$_1$-C$_3$ alkyl such as methyl; which can each be optionally substituted with a substituent selected from halogen, C$_1$-C$_3$ alkoxy, phenyl and oxetane.
E15. The compound of embodiment 6, wherein said oxetanyl, tetrahydrofuranyl or tetrathydropyranyl is optionally substituted with methyl.
E16. The compound of embodiment 1, wherein the compound is selected from the group consisting of:
6-benzyl-5-(cyclohexylmethyl)-1-tetrahydropyran-4-yl-pyrazolo[3, 4-d]pyrimidin-4-one;
5-(4-methoxybenzyl)-6-methyl-1-(tetrahydro-2H-pyran-4-yl)-1H-pyrazolo[3, 4-d]pyrimidin-4(5H)-one;
5-(cyclohexylmethyl)-6-methyl-1-tetrahydropyran-4-yl-pyrazolo[3, 4-d]pyrimidin-4-one;
5-[(4-methoxyphenyl)methyl]-6-methyl-1-propyl-pyrazolo[3, 4-d]pyrimidin-4-one;
5-(cyclohexylmethyl)-6-methyl-1-propyl-pyrazolo[3, 4-d]pyrimidin-4-one;
6-ethyl-5-[(4-methoxyphenyl)methyl]-1-tetrahydropyran-4-yl-pyrazolo[3, 4-d]pyrimidin-4-one;
6-(methoxymethyl)-5-[(4-methoxyphenyl)methyl]-1-tetrahydropyran-4-yl-pyrazolo[3, 4-d]pyrimidin-4-one;
6-isopropyl-5-[(4-methoxyphenyl)methyl]-1-tetrahydropyran-4-yl-pyrazolo[3, 4-d]pyrimidin-4-one;
5-[(4-methoxyphenyl)methyl]-6-(oxetan-3-ylmethyl)-1-tetrahydropyran-4-yl-pyrazolo[3, 4-d]pyrimidin-4-one;
5-[(3-fluorophenyl)methyl]-6-methyl-1-tetrahydropyran-4-yl-pyrazolo[4,3-c]pyridin-4-one;
5-[(2-fluorophenyl)methyl]-6-methyl-1-tetrahydropyran-4-yl-pyrazolo[4,3-c]pyridin-4-one;
5-[(4-chlorophenyl)methyl]-6-methyl-1-tetrahydropyran-4-yl-pyrazolo[4,3-c]pyridin-4-one;
5-benzyl-6-methyl-1-tetrahydropyran-4-yl-pyrazolo[4,3-c]pyridin-4-one;
5-[(3-chlorophenyl)methyl]-6-methyl-1-tetrahydropyran-4-yl-pyrazolo[4,3-c]pyridin-4-one;
5-[(4-fluorophenyl)methyl]-6-methyl-1-tetrahydropyran-4-yl-pyrazolo[4,3-c]pyridin-4-one;
6-methyl-5-(p-tolylmethyl)-1-tetrahydropyran-4-yl-pyrazolo[4,3-c]pyridin-4-one;

5-(1,3-benzodioxol-5-ylmethyl)-6-methyl-1-tetrahydropyran-4-yl-pyrazolo[4,3-c]pyridin-4-one;
5-[(6-methoxy-3-pyridyl)methyl]-6-methyl-1-tetrahydropyran-4-yl-pyrazolo[4,3-c]pyridin-4-one;
5-(4-methoxybenzyl)-6-methyl-1-(tetrahydro-2H-pyran-4-yl)-1,5-dihydro-4H-pyrazolo[4,3-c]pyridin-4-one;
5-(4-methoxybenzyl)-6-methyl-1-propyl-1,5-dihydro-4H-pyrazolo[4,3-c]pyridin-4-one;
1-isopropyl-5-[(4-methoxyphenyl)methyl]-6-methyl-pyrazolo[4,3-c]pyridin-4-one;
5-[(4-methoxyphenyl)methyl]-6-methyl-1-tetrahydrofuran-3-yl-pyrazolo[4,3-c]pyridin-4-one;
1-cyclopropyl-5-[(4-methoxyphenyl)methyl]-6-methyl-pyrazolo[4,3-c]pyridin-4-one;
1-ethyl-5-[(4-methoxyphenyl)methyl]-6-methyl-pyrazolo[4,3-c]pyridin-4-one;
5-[(4-methoxyphenyl)methyl]-6-methyl-1-tetrahydropyran-3-yl-pyrazolo[4,3-c]pyridin-4-one;
5-[(4-methoxyphenyl)methyl]-6-methyl-1-[(2S,3R)-2-methyltetrahydrofuran-3-yl]pyrazolo[4,3-c]pyridin-4-one;
5-[(4-methoxyphenyl)methyl]-6-methyl-1-[(2R,3R)-2-methyltetrahydrofuran-3-yl]pyrazolo[4,3-c]pyridin-4-one;
5-[(4-methoxyphenyl)methyl]-6-methyl-1-(oxetan-3-yl)pyrazolo[4,3-c]pyridin-4-one;
5-(4-methoxybenzyl)-6-methyl-1-(4-methyltetrahydro-2H-pyran-4-yl)-1,5-dihydro-4H-pyrazolo[4, 3-c]pyridin-4-one;
and pharmaceutically acceptable salts of any of these compounds.

E17. A compound of any one of embodiments 1-16, wherein said compound has a PDE1A, PDE1B or PDE1C $IC_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.

E18. A compound of any one of embodiments 1-17 for use in therapy.

E19. A compound according to any of embodiments 1-17, for use as a medicament.

E20. A pharmaceutical composition comprising a therapeutically effective amount of a compound of any one of embodiments 1-17 and one or more pharmaceutically acceptable carriers, diluents and excipients.

E21. A compound according to any of embodiments 1-17 for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E22. A method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to any of embodiments 1-17 to a patient in need thereof.

E23. Use of a compound according to any of embodiments 1-17, for the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

COMPOUNDS OF THE INVENTION

TABLE 1

Compounds of the invention

| Example | Compound | PDE1A, $IC_{50}$ (nM) | PDE1B, $IC_{50}$ (nM) | PDE1C, $IC_{50}$ (nM) | % inhibition of PDE9 at 10 microM |
|---|---|---|---|---|---|
| 1 | 6-benzyl-5-(cyclohexylmethyl)-1-tetrahydropyran-4-yl-pyrazolo[3,4-d]pyrimidin-4-one | 349 | 320 | 120 | 51 |
| 2 | 5-(4-methoxybenzyl)-6-methyl-1-(tetrahydro-2H-pyran-4-yl)-1H-pyrazolo[3,4-d]pyrimidin-4(5H)-one | 132 | 62 | 74 | 10 |
| 3 | 5-(cyclohexylmethyl)-6-methyl-1-tetrahydropyran-4-yl-pyrazolo[3,4-d]pyrimidin-4-one | 172 | 103 | 29 | 29 |

TABLE 1-continued

Compounds of the invention

| Example | Compound | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 4 | 5-[(4-methoxyphenyl)methyl]-6-methyl-1-propyl-pyrazolo[3,4-d]pyrimidin-4-one | 108 | 68 | 72 | 13 |
| 5 | 5-(cyclohexylmethyl)-6-methyl-1-propyl-pyrazolo[3,4-d]pyrimidin-4-one | 111 | 31 | 36 | −16 |
| 6 | 6-ethyl-5-[(4-methoxyphenyl)methyl]-1-tetrahydropyran-4-yl-pyrazolo[3,4-d]pyrimidin-4-one | 107 | 80 | 140 | 2 |
| 7 | 6-(methoxymethyl)-5-[(4-methoxyphenyl)methyl]-1-tetrahydropyran-4-yl-pyrazolo [3,4-d]pyrimidin-4-one | 325 | 181 | 345 | −12 |
| 8 | 6-isopropyl-5-[(4-methoxyphenyl)methyl]-1-tetrahydropyran-4-yl-pyrazolo[3,4-d]pyrimidin-4-one | 751 | 211 | 1324 | 7 |
| 9 | 5-[(4-methoxyphenyl)methyl]-6-(oxetan-3-ylmethyl)-1-tetrahydropyran-4-yl-pyrazolo[3,4-d]pyrimidin-4-one | nd | 58 | 165 | 12 |
| 10 | 5-[(3-fluorophenyl)methyl]-6-methyl-1-tetrahydropyran-4-yl-pyrazolo[4,3-c]pyridin-4-one | 1070 | 361 | 149 | 3 |
| 11 | 5-[(2-fluorophenyl)methyl]-6-methyl-1-tetrahydropyran-4-yl-pyrazolo[4,3-c]pyridin-4-one | 589 | 250 | 61 | 12 |
| 12 | 5-[(4-chlorophenyl)methyl]-6-methyl-1-tetrahydropyran-4-yl-pyrazolo[4,3-c]pyridin-4-one | 127 | 65 | 419 | 16 |
| 13 | 5-benzyl-6-methyl-1-tetrahydropyran-4-yl-pyrazolo[4,3-c]pyridin-4-one | 1264 | 309 | 135 | −18 |
| 14 | 5-[(3-chlorophenyl)methyl]-6-methyl-1-tetrahydropyran-4-yl-pyrazolo[4,3-c]pyridin-4-one | 1303 | 413 | 95 | −15 |
| 15 | 5-[(4-fluorophenyl)methyl]-6-methyl-1-tetrahydropyran-4-yl-pyrazolo[4,3-c]pyridin-4-one | 1240 | 258 | 204 | −13 |
| 16 | 6-methyl-5-(p-tolylmethyl)-1-tetrahydropyran-4-yl-pyrazolo[4,3-c]pyridin-4-one | 400 | 71 | 496 | −1 |
| 17 | 5-(1,3-benzodioxol-5-ylmethyl)-6-methyl-1-tetrahydropyran-4-yl-pyrazolo[4,3-c]pyridin-4-one | 429 | 154 | 662 | −2 |
| 18 | 5-[(6-methoxy-3-pyridyl)methyl]-6-methyl-1-tetrahydropyran-4-yl-pyrazolo[4,3-c]pyridin-4-one | 738 | 370 | 1167 | 9 |
| 19 | 5-(4-methoxybenzyl)-6-methyl-1-(tetrahydro-2H-pyran-4-yl)-1,5-dihydro-4H-pyrazolo[4,3-c]pyridin-4-one | 184 | 88 | 171 | 19 |
| 20 | 5-(4-methoxybenzyl)-6-methyl-1-propyl-1,5-dihydro-4H-pyrazolo[4,3-c]pyridin-4-one | 290 | 82 | 233 | 19 |
| 21 | 1-isopropyl-5-[(4-methoxyphenyl)methyl]-6-methyl-pyrazolo[4,3-c]pyridin-4-one | 49 | 37 | 134 | −14 |
| 22 | 5-[(4-methoxyphenyl)methyl]-6-methyl-1-tetrahydrofuran-3-yl-pyrazolo[4,3-c]pyridin-4-one | 1691 | 569 | 1205 | 8 |
| 23 | 1-cyclopropyl-5-[(4-methoxyphenyl)methyl]-6-methyl-pyrazolo[4,3-c]pyridin-4-one | 543 | 255 | 975 | −6 |
| 24 | 1-ethyl-5-[(4-methoxyphenyl)methyl]-6-methyl-pyrazolo[4,3-c]pyridin-4-one | 1115 | 329 | 1326 | 19 |
| 25 | 5-[(4-methoxyphenyl)methyl]-6-methyl-1-tetrahydropyran-3-yl-pyrazolo[4,3-c]pyridin-4-one | 825 | 113 | 644 | 8 |
| 26 | 5-[(4-methoxyphenyl)methyl]-6-methyl-1-[(2S,3R)-2-methyltetrahydrofuran-3-yl]pyrazolo[4,3-c]pyridin-4-one | 206 | 83 | 345 | 8 |

TABLE 1-continued

Compounds of the invention

| Example | Compound | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 27 | 5-[(4-methoxyphenyl)methyl]-6-methyl-1-[(2R,3R)-2-methyltetrahydrofuran-3-yl]pyrazolo[4,3-c]pyridin-4-one | 1303 | 179 | 686 | 13 |
| 28 | 5-[(4-methoxyphenyl)methyl]-6-methyl-1-(oxetan-3-yl)pyrazolo[4,3-c]pyridin-4-one | 63% inhibition @10 µM | 704 | 2185 | 14 |
| 29 | 5-(4-methoxybenzyl)-6-methyl-1-(4-methyltetrahydro-2H-pyran-4-yl)-1,5-dihydro-4H-pyrazolo[4,3-c]pyrid in-4-one | 119 | 87 | 174 | 26 | nd means "not determined"

Table 1 lists the IC$_{50}$ value for inhibition of PDE1 by the compounds of the invention. The IC$_{50}$ value refers to the concentration (nM) of the compound required to reach 50% inhibition of the PDE1 enzyme at the specified substrate concentration.

For comparative purpose, the table also lists % inhibition of PDE9 at 10 µM, which refers to the % inhibition of the PDE9 enzyme obtained at a concentration of 10 micro molar of the compound.

PDE1 and PDE9 assays are described in the Experimental Section.

EXPERIMENTAL SECTION

Preparation of the Compounds of the Invention—General Methods

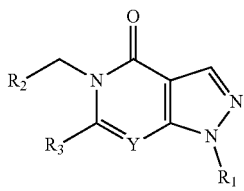
(I)

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those method described in standard reference books such as "Compendium of Organic Synthetic Methods, Vol. I-XIII" (published with Wiley-Interscience, ISSN: 1934-4783). Preferred methods include, but are not limited to, those described below.

The schemes are representative of methods useful in synthesising the compounds of the present invention. They are not to constrain the scope of the invention in any way.

Method 1:

Scheme 1

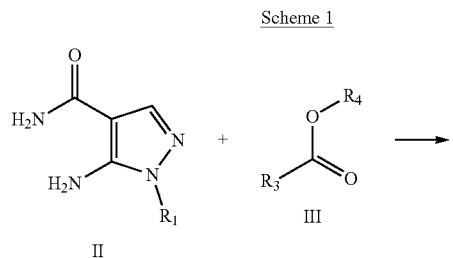

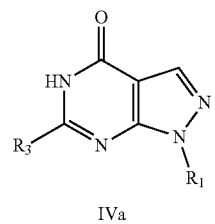
IVa where $R_1$ and $R_3$ are as described for formula I and $R_4$ is an alkyl group such as methyl or ethyl.

Compounds of general formula II (Scheme 1) can be prepared as described in the literature (J. Med. Chem. 2009, 52, 7949). Compounds of general formula IVa can be prepared from compounds of general formulae II and III as described in the literature (J. Med. Chem. 2009, 52, 7949).

Method 2:

Scheme 2

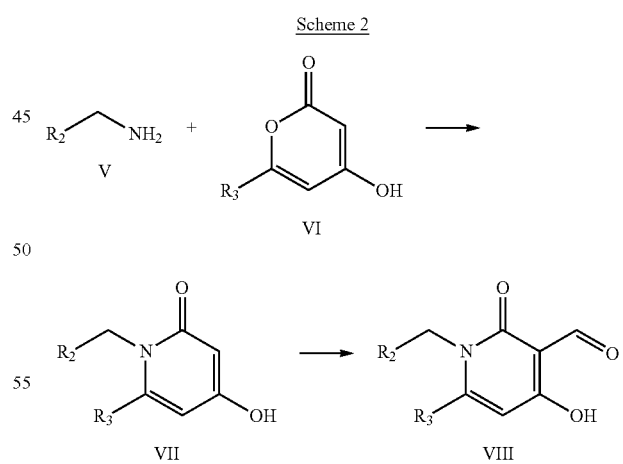

where $R_2$ and $R_3$ are as described for formula I.

Compounds of general formula VII (Scheme 2) can be prepared by heating a mixture of compounds of general formulae V and VI in a solvent such as water. Compounds of general formula VIII can be prepared by treating compounds of general formula VII with phosphoryl chloride and dimethyl formamide.

Method 3:

Scheme 3

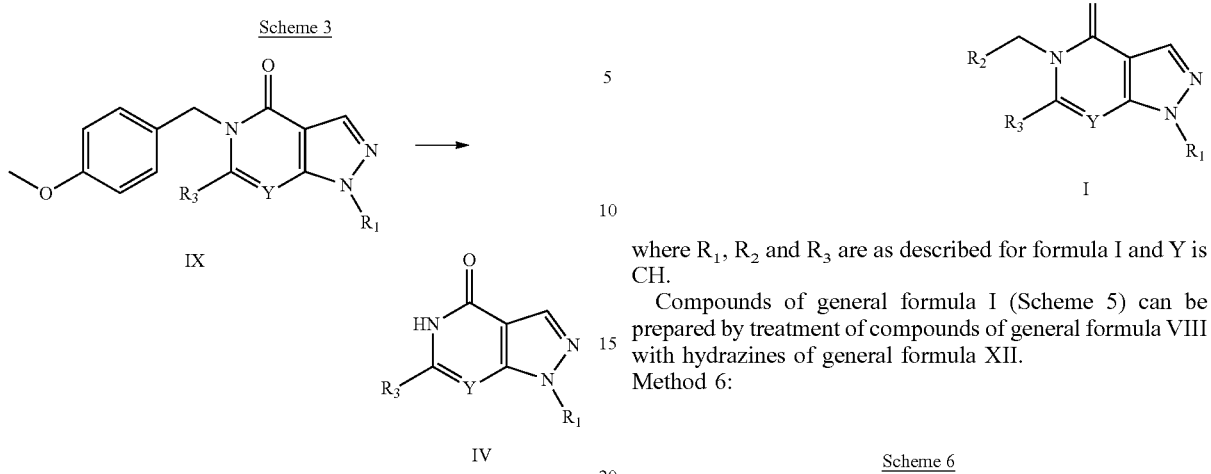

where $R_1$ and $R_3$ are as described for formula I.

Compounds of general formula IV (Scheme 3) can be prepared by treatment of compounds of general formula IX with an acid such as trifluoroacetic acid.

Method 4:

Scheme 4

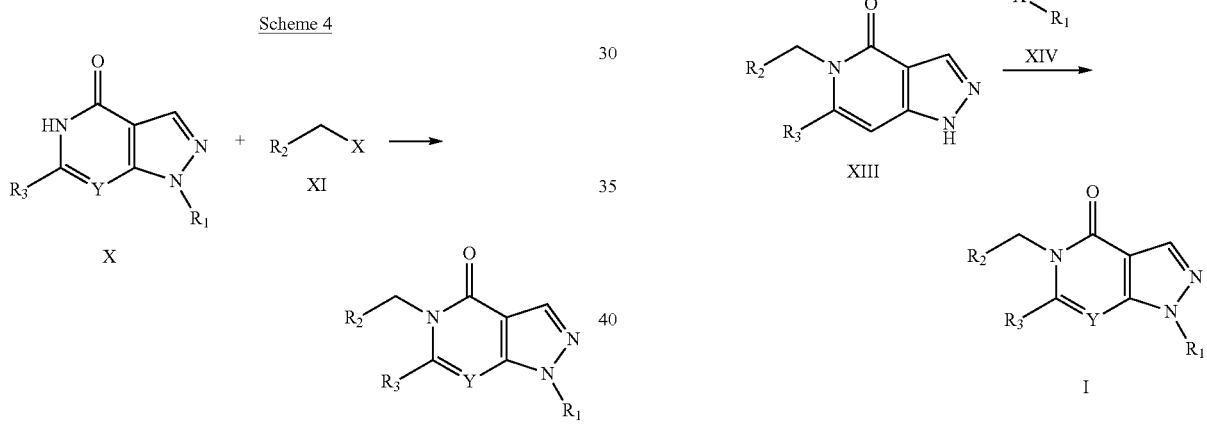

where $R_1$, $R_2$ and $R_3$ are as described for formula I and X is a leaving group such as but not limited to chloride, bromide, iodide or mesylate.

Compounds of general formula I (Scheme 4) can be prepared by treatment of compounds of general formula X with compounds of general formula XI in the presence of a base such as but not limited to potassium carbonate or cesium carbonate.

Method 5:

Scheme 5

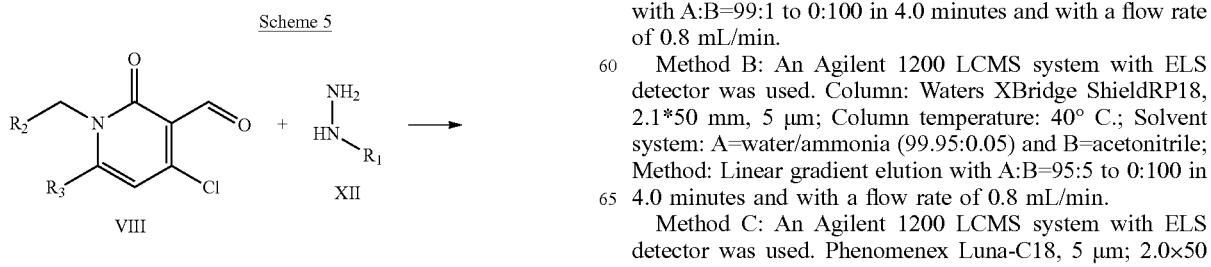

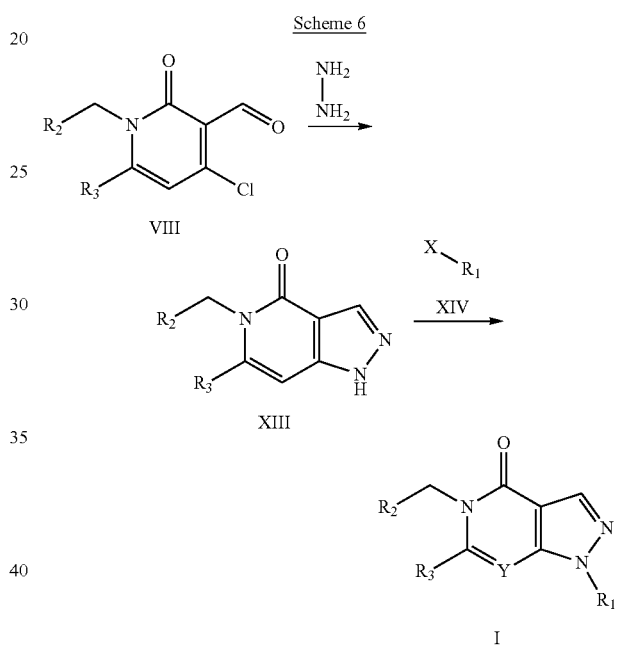

where $R_1$, $R_2$ and $R_3$ are as described for formula I and Y is CH.

Compounds of general formula I (Scheme 5) can be prepared by treatment of compounds of general formula VIII with hydrazines of general formula XII.

Method 6:

Scheme 6 where $R_1$, $R_2$ and $R_3$ are as described for formula I, X is a leaving group such as but not limited to chloride, bromide, iodide or mesylate and Y is CH.

Compounds of general formula I (Scheme 6) can be prepared by treatment of compounds of general formula VIII with hydrazine followed by alkylation with compounds of general formula XIV.

General Methods LC-MS Methods

Method A: An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method B: An Agilent 1200 LCMS system with ELS detector was used. Column: Waters XBridge ShieldRP18, 2.1*50 mm, 5 μm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method C: An Agilent 1200 LCMS system with ELS detector was used. Phenomenex Luna-C18, 5 μm; 2.0×50 mm; Column temperature: 50° C.; Solvent system: A=water/ trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method D: A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/minute.

Method E: A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5: 0.1); Method: Linear gradient elution with A:B=90:10 to 0:100 in 1.0 minutes and with a flow rate of 1.2 mL/minute.

Intermediates

Intermediate: 5-amino-1-(tetrahydro-2H-pyran-4-yl)-1H-pyrazole-4-carbonitrile

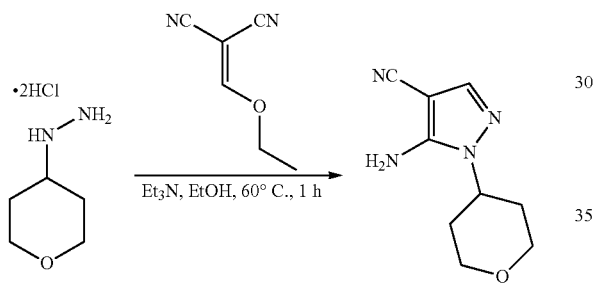

To a mixture of (tetrahydro-2H-pyran-4-yl)hydrazine dihydro chloride (5.0 g, 26 mmol) and Et₃N (5.62 g, 55.5 mmol) in EtOH (100 mL) was added 2-(ethoxymethylene) malononitrile (3.23 g, 26.4 mmol). The mixture was stirred at 60° C. for 1 hour. Solvent was removed under vacuum. The residue was washed with water (40 mL) then DCM (40 mL). The filter cake was dried under vacuum to give 5-amino-1-(tetrahydro-2H-pyran-4-yl)-1H-pyrazole-4-carbonitrile (2.3 g, 45% yield).

The following intermediate was prepared in a similar manner:
5-amino-1-cyclopropyl-1H-pyrazole-4-carbonitrile and 5-amino-1-propyl-1H-pyrazole-4-carbonitrile Intermediate: 5-amino-1-(tetrahydro-2H-pyran-4-yl)-1H-pyrazole-4-carboxamide

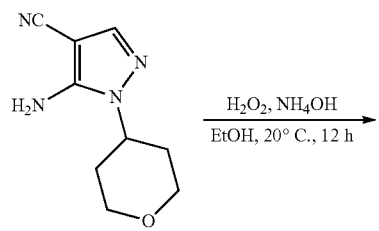

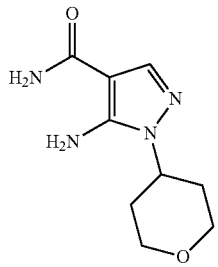

To a mixture of 5-amino-1-(tetrahydro-2H-pyran-4-yl)-1H-pyrazole-4-carbonitrile (2.3 g, 12 mmol) in EtOH (40 mL) were added H₂O₂ (10 mL) and NHa.H₂O in water (10 mL). The mixture was stirred at 20° C. for 12 hours. The mixture was quenched with 2N Na₂SO₃ (40 mL) and evaporated under vacuum. The residue was washed with water (20 mL×2). The filter cake was dried under vacuum to give 5-amino-1-(tetrahydro-2H-pyran-4-yl)-1H-pyrazole-4-carboxamide (1.3 g, 51% yield).

The following intermediates were prepared in a similar manner:
5-amino-1-cyclopropyl-1H-pyrazole-4-carboxamide; and
5-amino-1-propyl-1H-pyrazole-4-carboxamide Intermediate: 6-benzyl-1-(tetrahydro-2H-pyran-4-yl)-1,5-dihydro-4H-pyrazolo[3,4-d]pyrimidin-4-one

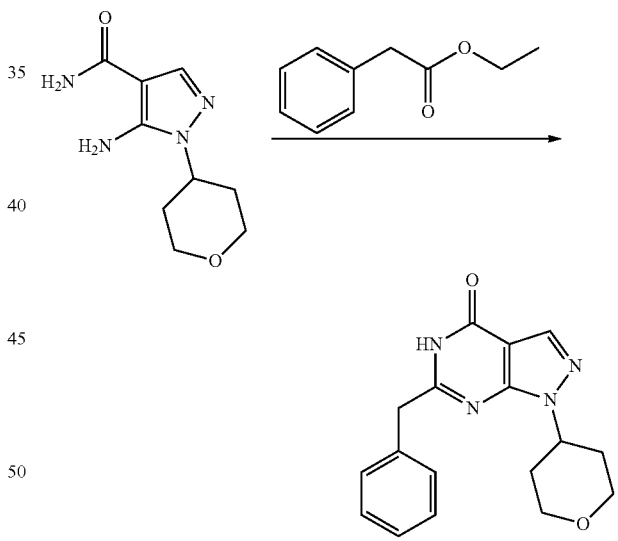

To a solution of 5-amino-1-(tetrahydro-2H-pyran-4-yl)-1H-pyrazole-4-carboxamide (100 mg, 0.47 mmol) and ethyl 2-phenylacetate (234 mg, 1.43 mmol) in EtOH (4 mL) was added NaOEt (97 mg, 1.43 mmol). The mixture was stirred at 140° C. for 1 hour under microwave conditions. Solvent was removed under vacuum. The residue was purified by prep TLC (DCM:MeOH=10:1) to give 6-benzyl-1-(tetrahydro-2H-pyran-4-yl)-1,5-dihydro-4H-pyrazolo[3,4-d]pyrimidin-4-one (120 mg, yield: 77%).

The following intermediate was prepared in a similar manner:
6-methyl-1-propyl-1,5-dihydro-4H-pyrazolo[3,4-d]pyrimidin-4-one

Intermediate: 6-methyl-1-(tetrahydro-2H-pyran-4-yl)-1,5-dihydro-4H-pyrazolo[3,4-d]pyrimidin-4-one

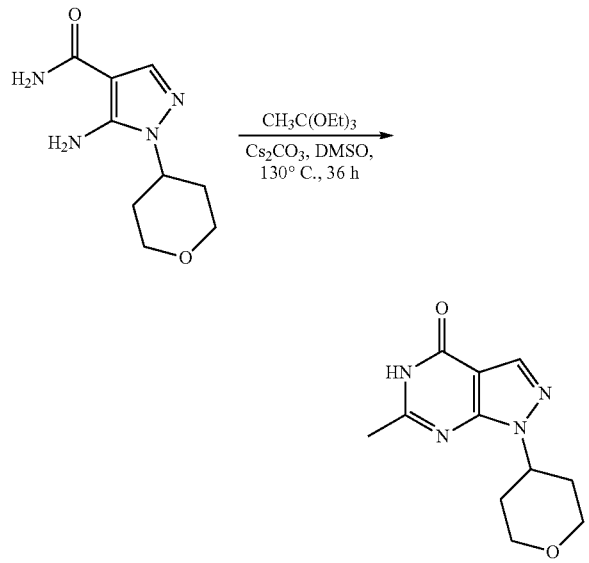

To a solution of 5-amino-1-(tetrahydro-2H-pyran-4-yl)-1H-pyrazole-4-carboxamide (1.0 g, 4.76 mmol) and triethyl orthoformate (7.72 g, 47.6 mmol) in DMSO (20 mL) was added $Cs_2CO_3$ (3.1 g 9.5 mmol). The mixture was stirred at 130° C. for 36 hours. The mixture was diluted with water (100 mL) and extracted with DCM (30 mL×3). The organic layer was washed with water (30 mL×2) and dried over $Na_2SO_4$. The organic layer was evaporated under vacuum. The mixture was purified by silica gel chromatography (DCM:MeOH from 20:1 to 5:1) to give 6-methyl-1-(tetrahydro-2H-pyran-4-yl)-1,5-dihydro-4H-pyrazolo[3,4-d]pyrimidin-4-one (560 mg, 50% yield).

The following intermediates were prepared in a similar manner:

6-methyl-1-propyl-1,5-dihydro-4H-pyrazolo[3,4-d]pyrimidin-4-one, prepared from 5-amino-1-propyl-1H-pyrazole-4-carboxamide and triethyl orthoformate;

6-ethyl-1-(tetrahydro-2H-pyran-4-yl)-1,5-dihydro-4H-pyrazolo[3,4-d]pyrimidin-4-one, prepared from 5-amino-1-(tetrahydro-2H-pyran-4-yl)-1H-pyrazole-4-carboxamide methyl propionate;

6-(methoxymethyl)-1-(tetrahydro-2H-pyran-4-yl)-1,5-dihydro-4H-pyrazolo[3,4-d]pyrimidin-4-one, prepared from 5-amino-1-(tetrahydro-2H-pyran-4-yl)-1H-pyrazole-4-carboxamide methyl 2-methoxyacetate;

6-isopropyl-1-(tetrahydro-2H-pyran-4-yl)-1,5-dihydro-4H-pyrazolo[3,4-d]pyrimidin-4-one, prepared from 5-amino-1-(tetrahydro-2H-pyran-4-yl)-1H-pyrazole-4-carboxamide methyl isobutyrate; and 6-(oxetan-3-ylmethyl)-1-(tetrahydro-2H-pyran-4-yl)-1,5-dihydro-4H-pyrazol o[3,4-d]pyrimidin-4-one, prepared from 5-amino-1-(tetrahydro-2H-pyran-4-yl)-1H-pyrazole-4-carboxamide methyl 2-(oxetan-3-yl)acetate.

Intermediate: 4-hydroxy-1-(4-methoxybenzyl)-6-methylpyridin-2(1H)-one

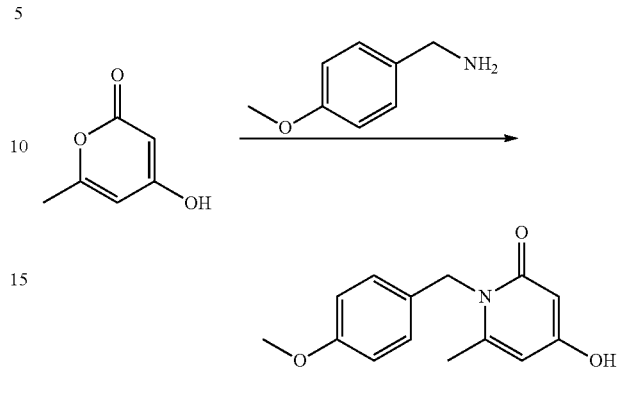

To a solution of 4-hydroxy-6-methyl-2H-pyran-2-one (12 g, 95 mmol) in $H_2O$ (200 mL) was added (4-methoxyphenyl)methanamine (13.05 g, 95.16 mmol). The mixture was stirred at 100° C. for 16 hours. A solid was obtained. The mixture was filtered. The filter cake was dried under vacuum to give 4-hydroxy-1-(4-methoxybenzyl)-6-methylpyridin-2(1H)-one (22.0 g, 63.7 mmol, 67% yield) which was used to the next step directly. $^1$H NMR (DMSO-$d_6$ 400 MHz): δ10.49 (br. s, 1H), 7.02 (d, J=8.4 Hz 2H), 6.85 (d, J=8.4 Hz, 2H), 5.74 (s, 1H), 5.55 (s, 1H), 5.07 (s, 2H), 3.68 (s, 3H), 2.14 (s, 3H).

Intermediate: 4-chloro-1-(4-methoxybenzyl)-6-methyl-2-oxo-1,2-dihydropyridine-3-carbaldehyde

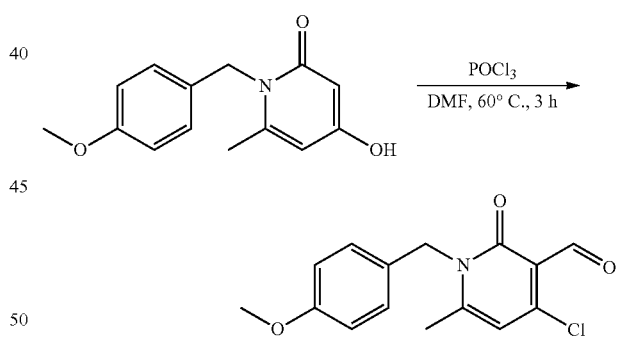

To a solution of 4-hydroxy-1-(4-methoxybenzyl)-6-methylpyridin-2(1H)-one (10 g, 29 mmol) in DMF (100 mL) was added $POCl_3$ (11.1 g, 72.4 mmol) dropwise. The resulting mixture was stirred at 60° C. for 3 hours. The mixture was poured into ice water (700 g) and extracted with ethyl acetate (500 ml×2). The organic layer was washed with water (500 mL×2) and brine (500 mL), dried over $Na_2SO_4$ and concentrated. The residue was purified by column chromatography on silica gel (40% ethyl acetate in petroleum ether) to give 4-chloro-1-(4-methoxybenzyl)-6-methyl-2-oxo-1,2-dihydropyridine-3-carbaldehyde (4.0 g, 8.2 mmol, 28% yield).

Intermediate: 6-methyl-1-(tetrahydro-2H-pyran-4-yl)-1,5-dihydro-4H-pyrazolo[4,3-c]pyridin-4-one

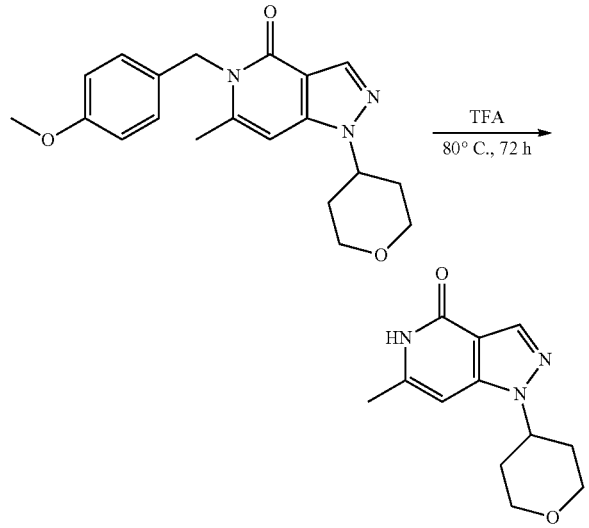

A solution of 5-(4-methoxybenzyl)-6-methyl-1-(tetrahydro-2H-pyran-4-yl)-1,5-dihydro-4H-pyrazolo[4,3-c]pyridin-4-one (1.30 g, 3.68 mmol) in TFA (40 mL) was stirred at 80-90° C. for 72 hours. The mixture was concentrated. The crude was purified by column chromatography on silica gel (using a gradient of petroleum ether and ethyl acetate) to give 6-methyl-1-(tetrahydro-2H-pyran-4-yl)-1,5-dihydro-4H-pyrazolo[4,3-c]pyridin-4-one (500 mg, 1.8 mmol, 48% yield).

Intermediate: tert-butyl 2-(propan-2-ylidene)hydrazine-1-carboxylate

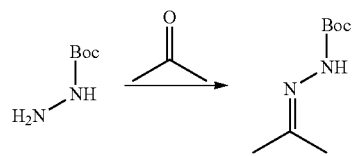

A solution of tert-butyl hydrazinecarboxylate (3.0 g, 23 mmol) in acetone (20 mL) was stirred at 20° C. for 16 hours. The mixture was concentrated to give tert-butyl 2-(propan-2-ylidene)hydrazine-1-carboxylate (3.9 g, 23 mmol, 99% yield).

$^1$H NMR (CDCl$_3$ 400 MHz): δ 7.33 (br. s, 1H), 2.02 (s, 3H), 1.80 (s, 3H), 1.50 (s, 9H).

Intermediate: tert-butyl 2-isopropylhydrazine-1-carboxylate

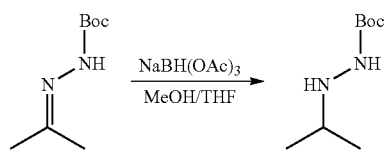

To a solution of tert-butyl 2-(propan-2-ylidene)hydrazine-1-carboxylate (3.90 g, 22.7 mmol) in THF (22 mL) and MeOH (22 mL) was added NaBH(OAc)$_3$ (4.80 g, 22.7 mmol) portionwise. The resulted mixture was refluxed under N$_2$ balloon for 2h and then cooled to 25° C. for 16 hours. The mixture was concentrated. The crude was purified by column chromatograph on silica gel (petroleum ether:ethyl acetate=4:1). The product was recrystallized by ethyl acetate and petroleum ether to give tert-butyl 2-isopropylhydrazine-1-carboxylate (400 mg, 2.30 mmol, 10% yield).

$^1$H NMR (CDCl$_3$ 400 MHz): δ 6.67 (br. s, 1H), 5.99-5.98 (m, 1H), 3.54-3.48 (m, 1H), 1.51 (s, 9H), 1.26 (d, J=6.8 Hz, 6H).

Intermediate: Isopropylhydrazine Hydrochloride

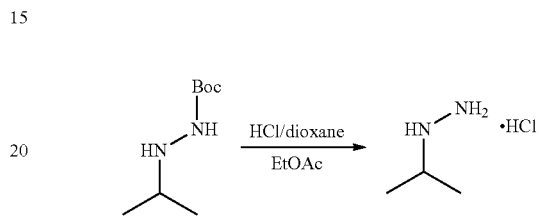

To a solution of tert-butyl 2-isopropylhydrazine-1-carboxylate (400 mg, 2.30 mmol) in ethyl acetate (5 mL) was added HCl/dioxane (5 mL). The resulted mixture was stirred at 20° C. for 16 hours. The mixture was concentrated to give isopropylhydrazine hydrochloride (300 mg) which was used to the next step directly.

Intermediate: tert-butyl 2-(dihydrofuran-3(2H)-ylidene)hydrazine-1-carboxylate

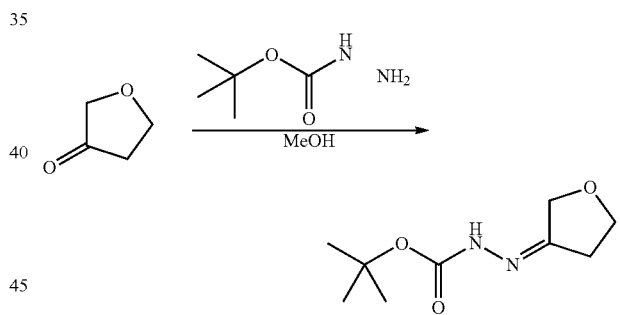

A solution of dihydrofuran-3(2H)-one (5.0 g, 58 mmol) and tert-butyl hydrazinecarboxylate (7.68 g, 58.08 mmol) in MeOH (50 mL) was stirred at 15° C. for 2 hours. The mixture was concentrated to remove MeOH and afford tert-butyl 2-(dihydrofuran-3(2H)-ylidene)hydrazine-1-carboxylate (11 g, 55 mmol, 95% yield).

$^1$H NMR (MeOD 400 MHz): δ4.19 (s, 2H), 4.03 (t, J=6.8 Hz, 2H), 2.53 (t, J=7.2 Hz, 2H), 1.50 (s, 9H).

Intermediate: tert-butyl 2-(tetrahydrofuran-3-yl)hydrazine-1-carboxylate

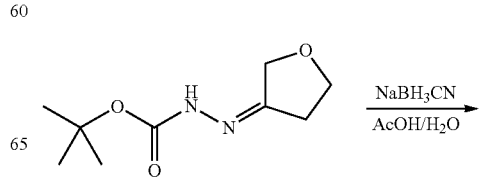

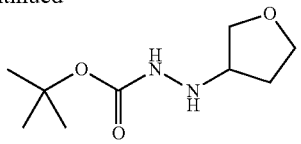

A solution of tert-butyl 2-(dihydrofuran-3(2H)-ylidene)hydrazine-1-carboxylate (11 g, 55 mmol) in AcOH (30 mL) and H₂O (60 mL) was stirred at 15° C. for 0.5 hours. Then NaBH₃CN (3.80 g, 60.4 mmol) was added to the solution in portions. The resulted mixture was stirred at 15° C. for 2 hours. The mixture was neutralized with 2M NaOH (500 mL) and extracted with DCM (100 mL×3), the organic layer was washed with brine (300 mL×3), dried with anhydrous Na₂SO₄, filtrated and concentrated. The crude was purified by column chromatography on silica gel (ethyl acetate) to afford the tert-butyl 2-(tetrahydrofuran-3-yl)hydrazine-1-carboxylate (11 g, crude).

Intermediate: (tetrahydrofuran-3-yl)hydrazine hydrochloride

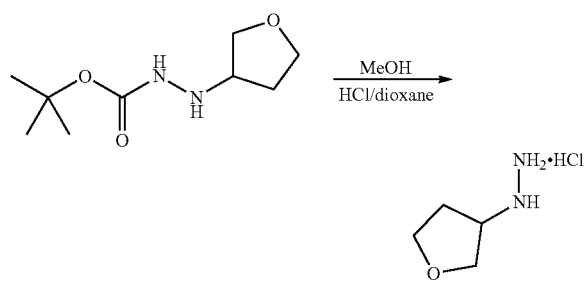

To a solution of tert-butyl 2-(tetrahydrofuran-3-yl)hydrazine-1-carboxylate (2.0 g, 9.9 mmol) in MeOH (50 mL) was added HCl/dioxane (4 M, 9.1 mL) dropwise. The solution was stirred at 0° C. for 2 hours. The mixture was filtrated to remove the solvent and afford the (tetrahydrofuran-3-yl)hydrazine hydrochloride (1 g).

Intermediate: di-tert-butyl 1-cyclopropylhydrazine-1,2-dicarboxylate

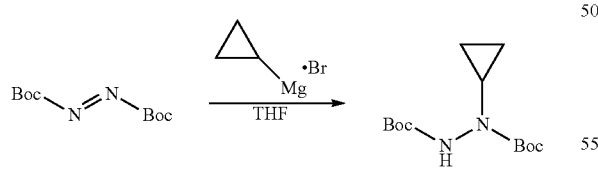

To a solution of cyclopropylmagnesium bromide (0.5 M, 11.02 mL) in THF (10 mL) was added di-tert-butyl azadicarboxylate (1.27 g, 5.51 mmol) at −78° C. under argon. The mixture was stirred at −78° C. for 0.5 hour. The reaction mixture was quenched by addition NH₄Cl (sat.aq. 10 mL) at 0° C., and then diluted with H₂O (60 mL) and extracted with ethyl acetate (100 mL×2). The combined organic layers were washed with brine (50 mL), dried over Na₂SO₄, filtered and concentrated under reduced pressure to give a residue. The residue was purified by flash silica gel chromatography (using a gradient of ethyl acetate and petroleum ether) to give di-tert-butyl 1-cyclopropylhydrazine-1,2-dicarboxylate (1.20 g, 4.41 mmol, 80% yield. ¹H NMR (MeOD 400 MHz): δ 2.84-2.92 (m, 1H), 1.46 (s, 18H), 0.67 (s, 4H).

Intermediate: Cyclopropylhydrazine Hydrochloride

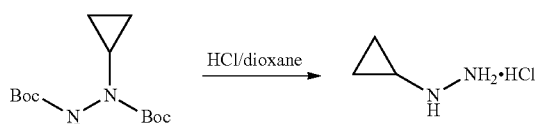

Di-tert-butyl 1-cyclopropylhydrazine-1,2-dicarboxylate (1.20 g, 4.41 mmol) was dissolved in HCl/dioxane (10 mL). The mixture was stirred at 15° C. for 12 hours. The reaction mixture was concentrated under reduced pressure to give cyclopropylhydrazine hydrochloride (0.45 g, 4.14 mmol, 94% yield). ¹H NMR (MeOD 400 MHz): δ2.58-2.63 (m, 1H), 0.60-0.70 (m, 4H).

Intermediate: 5-(4-methoxybenzyl)-6-methyl-1,5-dihydro-4H-pyrazolo[4,3-c]pyridin-4-one

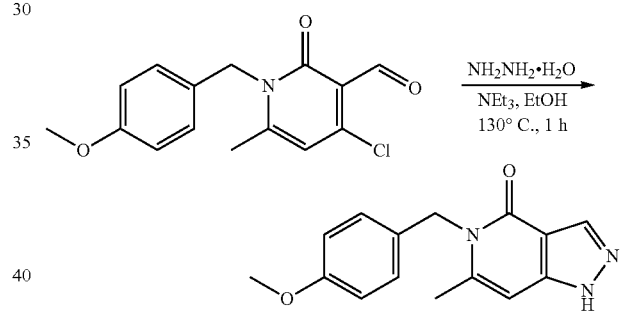

A mixture of NH₂NH₂·H₂O (35 mg, 0.69 mmol), 4-chloro-1-(4-methoxybenzyl)-6-methyl-2-oxo-1,2-dihydropyridine-3-carbaldehyde (200 mg, 0.69 mmol) and triethylamine (208 mg, 2.06 mmol) in EtOH (3 mL) was stirred at 130° C. under microwave irradiation for 1 hour. The mixture was concentrated and the crude was purified by preparative TLC (ethyl acetate) to give 5-(4-methoxybenzyl)-6-methyl-1,5-dihydro-4H-pyrazolo[4,3-c]pyridin-4-one (130 mg, 0.472 mmol, 69% yield).

Intermediate: benzyl 2-(2-methyldihydrofuran-3(2H)-ylidene)hydrazine-1-carboxylate

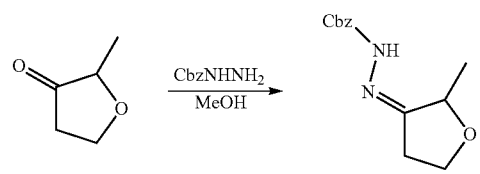

A solution of 2-methyldihydrofuran-3(2H)-one (5.0 g, 50 mmol) and benzyl N-aminocarbamate (8.3 g, 50 mmol) in dry MeOH (150 mL) was stirred at 15° C. for 16 hours. The mixture was concentrated to give benzyl 2-(2-methyldihydrofuran-3(2H)-ylidene)hydrazine-1-carboxylate (12 g, 97% yield)

Intermediates: benzyl 2-(cis-2-methyltetrahydrofuran-3-yl)hydrazine-1-carboxylate and benzyl 2-(trans-2-methyltetrahydrofuran-3-yl)hydrazine-1-carboxylate

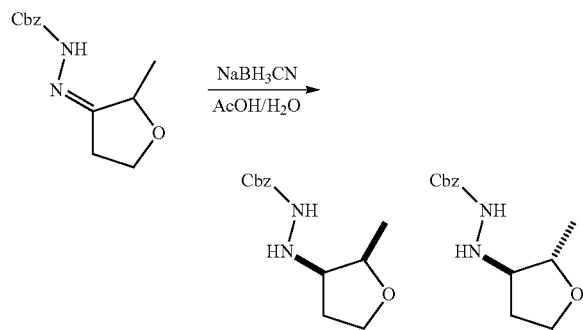

To a solution of benzyl 2-(2-methyldihydrofuran-3(2H)-ylidene)hydrazine-1-carboxylate (12 g, 48 mmol,) in $H_2O$ (96 mL) was added AcOH (40 mL). The mixture was stirred at 15° C. for 1 hour. Then $NaBH_3CN$ (3.34 g, 53.2 mmol) was added in small portions. The mixture was stirred at 15° C. for 2 hours. The mixture was adjusted to pH=8 by 5 N NaOH (aq). The mixture was extracted with ethyl acetate (200 mL×2). The combined organic layers were washed with $H_2O$ (200 mL), brine (200 mL), dried over $Na_2SO_4$, filtered and concentrated. The crude product was purified by flash chromatography on silica gel (using a gradient of ethyl acetate and petroleum ether) to give a mixture of benzyl 2-(cis-2-methyltetrahydrofuran-3-yl)hydrazine-1-carboxylate and benzyl 2-(trans-2-methyltetrahydrofuran-3-yl)hydrazine-1-carboxylate (6.0 g, 50% yield). 2 g of the mixture was purified by SFC twice to give benzyl 2-(trans-2-methyltetrahydrofuran-3-yl)hydrazine-1-carboxylate (700 mg, 32.5% yield) (Rt=5.671 min ($1^{st}$ run), 5.754 min ($2^{nd}$ run))$^1$H NMR ($CDCl_3$ 400 MHz): δ 7.35 (s, 5H), 6.23 (s, 1H), 5.13 (s, 2H), 3.99-3.97 (m, 2H), 3.85-3.84 (m, 1H), 3.74-3.68 (m, 1H), 3.59 (bs, 1H), 2.10-2.08 (m, 1H), 1.88-1.87 (m, 1H), 1.28 (d, J=6.0 Hz, 3H).

and benzyl 2-(cis-2-methyltetrahydrofuran-3-yl)hydrazine-1-carboxylate (450 mg, 20.7% yield) (Rt=8.354 min). $^1$H NMR ($CDCl_3$ 400 MHz): δ 7.35 (s, 5H), 6.22 (s, 1H), 5.13 (s, 2H), 3.99-3.97 (m, 2H), 3.87-3.86 (m, 1H), 3.74-3.68 (m, 1H), 3.59 (bs, 1H), 2.10-2.07 (m, 1H), 1.88-1.87 (m, 1H), 1.28 (d, J=6.0 Hz, 3H).

SFC condition 1: Instrument: SFC-80-(8); Column: AD 250 mm×30 mm, 5 μm; Mobile phase: A: Supercritical $CO_2$, B: EtOH (0.1% $NH_3H_2O$), A:B=70:30 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm SFC condition 2: Instrument: MG-II; Column: AY250 mm×30 mm, 10 μm; Mobile phase: A: Supercritical $CO_2$, B: EtOH (0.1% $NH_3H_2O$), A:B=75:25 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm Intermediate: cis-(2-methyltetrahydrofuran-3-yl)hydrazine hydrochloride

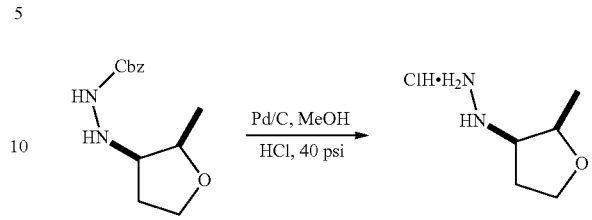

To a solution of benzyl 2-(cis-2-methyltetrahydrofuran-3-yl)hydrazine-1-carboxylate (800 mg, 3.20 mmol) in MeOH (20 mL) was added 1 M HCl (1 M, 9.6 mL) and Pd/C (500 mg) (wet, 10% Pd with 50% of water) under $N_2$. The suspension was degassed under vacuum and purged with $H_2$ several times. The mixture was stirred at 25° C. under $H_2$ (40 psi) for 16 hours. The mixture was filtered through celite and the filtrate was concentrated to give cis-(2-methyltetrahydrofuran-3-yl)hydrazine hydrochloride (450 mg, 92% yield) $^1$H NMR (DMSO $d_6$ 400 MHz): δ 8.55 (bs, 1H), 8.18 (bs, 1H), 7.43-7.18 (m, 1H), 3.88-3.79 (m, 2H), 3.57-3.51 (m, 2H), 2.06-2.02 (m, 2H), 1.10 (d, J=6.4 Hz, 3H).

Intermediate: tert-butyl 2-(dihydro-2H-pyran-3(4H)-ylidene)hydrazine-1-carboxylate

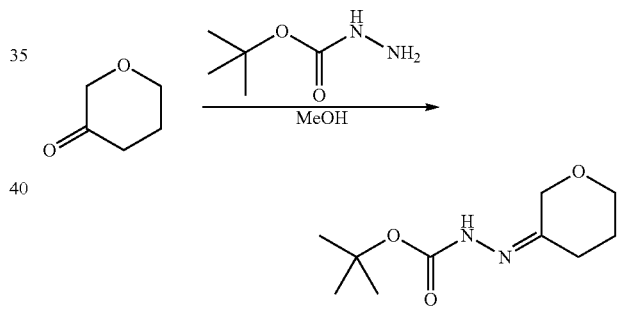

A solution of tert-butyl hydrazinecarboxylate (6.6 g, 50 mmol) and dihydro-2H-pyran-3(4H)-one (5 g, 50 mmol) in MeOH (50 mL) was stirred at 15° C. for 2 hours. The mixture was concentrated to remove MeOH and the crude was purified by column chromatography on silica gel (petroleum ether:ethyl acetate=1:1) to afford tert-butyl 2-(dihydro-2H-pyran-3(4H)-ylidene)hydrazine-1-carboxylate (10 g, 47 mmol, 93% yield).

Intermediate: tert-butyl 2-(tetrahydro-2H-pyran-3-yl)hydrazine-1-carboxylate

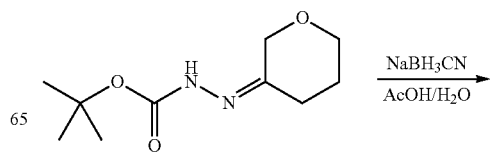

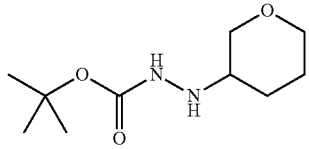

A mixture of tert-butyl 2-(dihydro-2H-pyran-3(4H)-ylidene)hydrazine-1-carboxylate (10 g, 47 mmol) in AcOH (50 mL) and H$_2$O (100 mL) was stirred at 15° C. for 0.5 hours. Then NaBH$_3$CN (3.23 g, 51 mmol) was added to the solution. The resulted mixture was stirred at 15° C. for 2 hours. The mixture was basified with 2M NaOH (aq) (200 mL) and extracted with DCM (100 mL×3), the organic layer was washed with brine (200 mL), dried with anhydrous Na$_2$SO$_4$, filtrated and concentrated to afford the crude product. The crude was purified by column chromatography on silica gel (ethyl acetate) to afford tert-butyl 2-(tetrahydro-2H-pyran-3-yl)hydrazine-1-carboxylate (9 g).

Intermediate: (tetrahydro-2H-pyran-3-yl)hydrazine hydrochloride

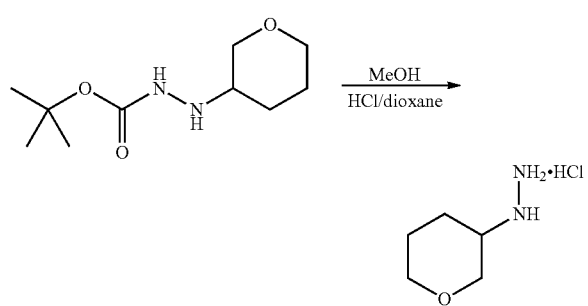

To a solution of tert-butyl 2-(tetrahydro-2H-pyran-3-yl)hydrazine-1-carboxylate (550 mg, 2.54 mmol) in MeOH (10 mL) and ethyl acetate (10 mL) was added HCl/MeOH (20 mL). The resulted mixture was stirred at 10° C. for 3 hours. The mixture was concentrated to give (tetrahydro-2H-pyran-3-yl)hydrazine hydrochloride (500 mg) which was used to the next step directly.

Intermediate: 4-isocyanato-4-methyltetrahydro-2H-pyran

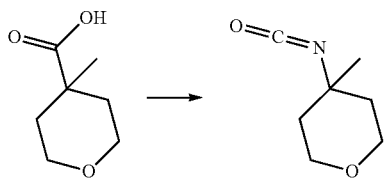

To a solution of compound 4-methyltetrahydro-2H-pyran-4-carboxylic acid (4.00 g, 27.8 mmol) and triethylamine (4.21 g, 41.6 mmol, 5.77 mL in toluene (100 mL) was added DPPA (8.40 g, 30.53 mmol, 6.61 mL). The mixture was stirred at 85° C. for 2h. The reaction mixture was treated with 1M NaOH(aq) (50 mL), extracted with EtOAc (100 mL*2). The organic layer was washed with brine (20 mL) and dried over Na$_2$SO$_4$ and concentrated in vacuo to give 4-isocyanato-4-methyltetrahydro-2H-pyran (2 g).

Intermediate: 4-methyltetrahydro-2H-pyran-4-amine

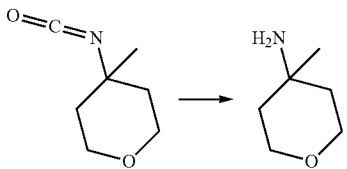

To a solution of compound 4-isocyanato-4-methyltetrahydro-2H-pyran (3.00 g, 21 mmol, 1 eq) in THF (20 mL) was added 5M HCl (aq) (20 mL). The mixture was stirred at 10-15° C. for 16 hours. The mixture was concentrated in vacuo, and dissolved in dichloromethane (30 mL) and filtered. The filter cake was dried to give 4-methyltetrahydro-2H-pyran-4-amine hydrochloride. To a suspension of 4-methyltetrahydro-2H-pyran-4-amine hydrochloride (200 mg, 1.32 mmol, 1 eq) in dichloromethane (5 mL) was added ion exchange resin (100 mg). The mixture was stirred at 15-20° C. for 5 min. The mixture was filtered and the filtrate was used for next step directly. A solution of 4-methyltetrahydro-2H-pyran-4-amine in dichloromethane (5 mL) was obtained.

Intermediate: tert-butyl 2-(4-methyltetrahydro-2H-pyran-4-yl)hydrazine-1-carboxylate

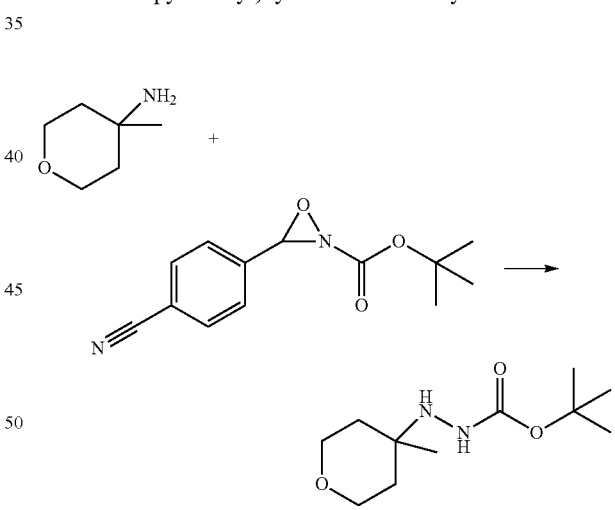

To a solution of tert-butyl 3-(4-cyanophenyl)-1,2-oxaziridine-2-carboxylate (Journal of Organic Chemistry, 58(18), 4791, 1993) (1 eq) in dichloromethane (5 mL) was added 4-methyltetrahydro-2H-pyran-4-amine (200 mg, 0.81 mmol). The mixture was stirred at 15-20° C. for 16 hours and at reflux (50° C.) for 4 hours. The reaction mixture was diluted with dichloromethane (20 mL), washed with water (20 mL) and brine (10 mL), dried over Na$_2$SO$_4$ and concentrated in vacuo. The residue was purified by silica gel chromatography (petroleum ether:ethyl acetate=1:1) to give tert-butyl 2-(4-methyltetrahydro-2H-pyran-4-yl)hydrazine-1-carboxylate (100 mg)

Intermediate: (4-methyltetrahydro-2H-pyran-4-yl)hydrazine hydrochloride

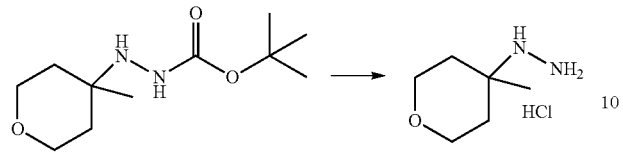

A solution of tert-butyl 2-(4-methyltetrahydro-2H-pyran-4-yl)hydrazine-1-carboxylate (100 mg, 0.30 mmol, 1 eq) in HCl in ethyl acetate (5 mL) was stirred at 15-20° C. for 1 hour. The mixture was filtered and the filter cake was washed with ethyl acetate (2×10 mL) and dried to give (4-methyltetrahydro-2H-pyran-4-yl)hydrazine hydrochloride (30 mg)

COMPOUNDS OF THE INVENTION

Example 1: 6-benzyl-5-(cyclohexyl methyl)-1-(tetrahydro-2H-pyran-4-yl)-1,5-dihydro-4H-pyrazolo[3,4-d]pyrimidin-4-one

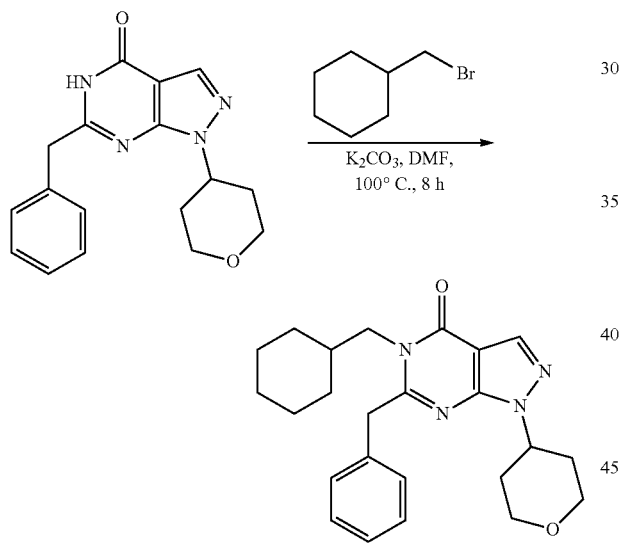

To a solution of 6-benzyl-1-(tetrahydro-2H-pyran-4-yl)-1,5-dihydro-4H-pyrazolo[3,4-d]pyrimidin-4-one (200 mg, 0.64 mmol) and (bromomethyl)cyclohexane (137 mg, 0.77 mmol) in DMF (2 mL) was added $K_2CO_3$ (178 mg, 1.29 mmol). The mixture was stirred at 100° C. for 8 hours. The mixture was diluted with ethyl acetate (10 mL) and washed with water (3 mL×2). The organic layer was dried over $Na_2SO_4$ and evaporated. The residue was purified by preparative TLC (DCM: ethyl acetate) to give 6-benzyl-5-(cyclohexylmethyl)-1-(tetrahydro-2H-pyran-4-yl)-1,5-dihydro-4H-pyrazolo[3,4-d]pyrimidin-4-one (20 mg, yield: 7%).

$^1$H NMR (CDCl$_3$, 400 MHz): δ 8.05 (m, 2H), 7.53-7.28 (m, 3H), 7.18 (d, J=6.8 Hz, 2H), 4.87-4.79 (m, 1H), 4.24 (s, 1H), 4.16-4.12 (m, 2H), 3.91-3.83 (bs, 2H), 3.60 (t, J=7.6 Hz, 2H), 2.45-2.36 (m, 2H), 1.97-1.94 (m, 2H), 1.74-1.63 (m, 7H), 1.17-1.09 (m, 4H). LC-MS: $t_R$=3.24 min (Method A), m/z=407.2 (MH$^+$).

The following compounds were prepared in a similar manner:

Example 2: 5-(4-methoxybenzyl)-6-methyl-1-(tetrahydro-2H-pyran-4-yl)-1H-pyrazolo[3,4-d]pyrimidin-4(5H)-one

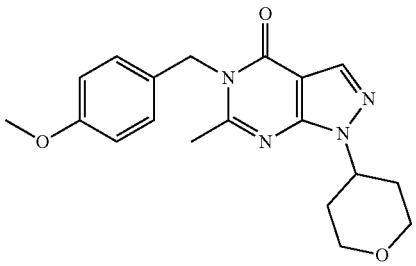 [SMILES: COc1ccc(Cn2c(C)nc3c(cnn3C3CCOCC3)c2=O)cc1]

Prepared from 6-methyl-1-(tetrahydro-2H-pyran-4-yl)-1,5-dihydro-4H-pyrazolo[3,4-d]pyrimidin-4-one and 1-(chloromethyl)-4-methoxybenzene.

$^1$HNMR (CDCl$_3$, 400 MHz): δ 8.10 (s, 1H), 7.14 (d, J=8.4, 2H), 6.86 (d, J=8.4, 2H), 5.30 (s, 2H), 4.86-4.79 (m, 1H), 4.17-4.13 (m, 2H), 3.79 (s, 3H), 3.63-3.58 (m, 2H), 2.55 (s, 3H), 2.45-2.36 (m, 2H), 1.94-1.90 (m, 2H). LC-MS (m/z) 355.1 (MH$^+$); $t_R$=0.61 (Method D)

Example 3: 5-(cyclohexylmethyl)-6-methyl-1-tetrahydropyran-4-yl-pyrazolo[3,4-d]pyrimidin-4-one

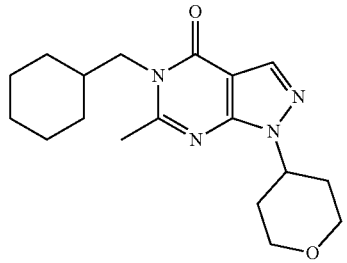 [SMILES: Cc1nc2c(cnn2C2CCOCC2)c(=O)n1CC1CCCCC1]

Prepared from 6-methyl-1-(tetrahydro-2H-pyran-4-yl)-1,5-dihydro-4H-pyrazolo[3,4-d]pyrimidin-4-one and (bromomethyl)cyclohexane.

$^1$HNMR (CDCl$_3$, 400 MHz): δ 8.03 (s, 1H), 4.85-4.77 (m, 1H), 4.16-4.13 (m, 2H), 3.93 (bs, 2H), 3.64-3.58 (m, 2H), 2.63 (s, 3H), 2.44-2.35 (m, 2H), 1.93-1.65 (m, 8H), 1.20-1.09 (m, 5H). LC-MS (m/z) 331.2 (MH$^+$); $t_R$=2.63 (Method C)

Example 4: 5-[(4-methoxyphenyl)methyl]-6-methyl-1-propyl-pyrazolo[3,4-d]pyrimidin-4-one

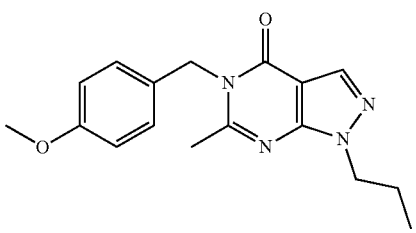 [SMILES: CCCn1ncc2c(=O)n(Cc3ccc(OC)cc3)c(C)nc21]

Prepared from 6-methyl-1-propyl-1,5-dihydro-4H-pyrazolo[3,4-d]pyrimidin-4-one and 1-(chloromethyl)-4-methoxybenzene.

¹HNMR (CDCl₃, 400 MHz): δ 8.08 (s, 1H), 7.14 (d, J=8.4 Hz 2H), 6.86 (d, J=8.4 Hz 2H), 5.30 (bs, 2H), 4.27 (t, J=7.2 Hz, 2H), 3.79 (s, 3H), 2.55 (s, 3H), 1.97-1.92 (m, 2H), 0.94 (t, J=7.2 Hz, 3H). LC-MS (m/z) 313.1 (MH⁺); $t_R$=2.54 (Method C)

Example 5: 5-(cyclohexylmethyl)-6-methyl-1-propyl-pyrazolo[3,4-d]pyrimidin-4-one

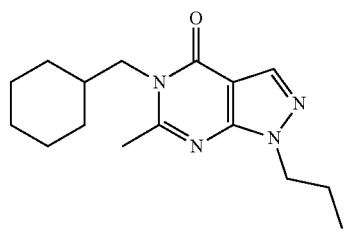 [SMILES: CCCn1ncc2c(=O)n(CC3CCCCC3)c(C)nc21]

Prepared from 6-methyl-1-propyl-1,5-dihydro-4H-pyrazolo[3,4-d]pyrimidin-4-one and (bromomethyl)cyclohexane.

¹HNMR (CDCl₃, 400 MHz): δ8.02 (s, 1H), 4.25 (t, J=7.2 Hz, 2H), 3.93 (bs, 2H), 2.63 (s, 3H), 1.96-1.91 (m, 2H), 1.74-1.65 (m, 6H), 1.20-1.09 (m, 5H), 0.94 (t, J=7.2 Hz, 3H). LC-MS (m/z) 289.2 (MH⁺); $t_R$=2.84 (Method C)

Example 6: 6-ethyl-5-[(4-methoxyphenyl)methyl]-1-tetrahydropyran-4-yl-pyrazolo[3,4-d]pyrimidin-4-one

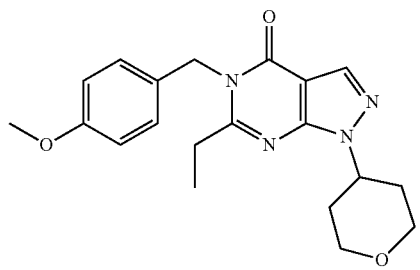 [SMILES: CCc1nc2c(cnn2C2CCOCC2)c(=O)n1Cc1ccc(OC)cc1]

Prepared from 6-ethyl-1-(tetrahydro-2H-pyran-4-yl)-1,5-dihydro-4H-pyrazolo[3,4-d]pyrimidin-4-one and 1-(chloromethyl)-4-methoxybenzene.

¹H NMR (CDCl₃ 400 MHz): δ 8.07 (s, 1H), 7.10 (d, J=8.4 Hz, 2H), 6.83 (d, J=8.4 Hz, 2H), 5.30 (bs, 2H), 4.84-4.78 (m, 1H), 4.15-4.13 (m, 2H), 3.76 (s, 3H), 3.60 (t, J=12.0 Hz, 2H), 2.77 (q, J=7.6 Hz, 2H), 2.46-2.36 (m, 2H), 1.95-1.92 (m, 2H), 1.28 (t, J=6.8 Hz, 3H). LC-MS (m/z) 369.2 (MH⁺); $t_R$=2.34 (Method B).

Example 7: 6-(methoxymethyl)-5-[(4-methoxyphenyl)methyl]-1-tetrahydropyran-4-yl-pyrazolo[3,4-d]pyrimidin-4-one

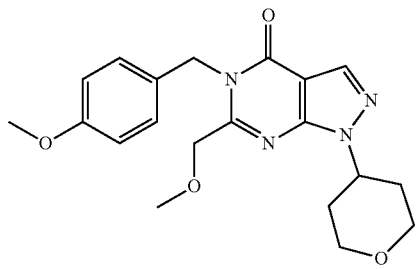 [SMILES: COCc1nc2c(cnn2C2CCOCC2)c(=O)n1Cc1ccc(OC)cc1]

Prepared from 6-(methoxymethyl)-1-(tetrahydro-2H-pyran-4-yl)-1,5-dihydro-4H-pyrazolo[3,4-d]pyrimidin-4-one and 1-(chloromethyl)-4-methoxybenzene.

¹H NMR (CDCl₃ 400 MHz): δ 8.11 (s, 1H), 7.14 (d, J=8.4 Hz, 2H), 6.84 (d, J=7.6 Hz, 2H), 5.46 (s, 2H), 4.88-4.83 (m, 1H), 4.43 (s, 2H), 4.15-4.12 (m, 2H), 3.77 (s, 3H), 3.60 (t, J=12.0 Hz, 2H), 3.46 (s, 3H), 2.45-2.34 (m, 2H), 1.92 (d, J=12.0 Hz, 2H). LC-MS (m/z) 385.2 (MH⁺); $t_R$=2.42 (Method C).

Example 8: 6-isopropyl-5-[(4-methoxyphenyl)methyl]-1-tetrahydropyran-4-yl-pyrazolo[3,4-d]pyrimidin-4-one

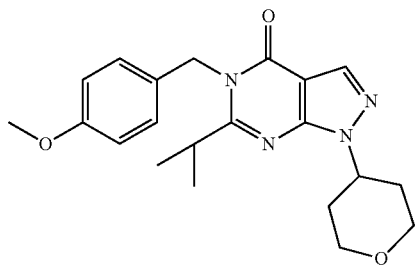 [SMILES: COc1ccc(Cn2c(C(C)C)nc3c(cnn3C3CCOCC3)c2=O)cc1]

Prepared from 6-isopropyl-1-(tetrahydro-2H-pyran-4-yl)-1,5-dihydro-4H-pyrazolo[3,4-d]pyrimidin-4-one and 1-(chloromethyl)-4-methoxybenzene.

¹H NMR (CDCl₃ 400 MHz): δ 8.07 (s, 1H), 7.08 (d, J=8.8 Hz, 2H), 6.85 (d, J=8.4 Hz, 2H), 5.36 (bs, 2H), 4.84-4.78 (m, 1H), 4.17-4.13 (m, 2H), 3.78 (s, 3H), 3.64-3.58 (m, 2H), 3.18-3.13 (m, 1H), 2.47-2.38 (m, 2H), 1.98-1.94 (m, 2H), 1.24-1.22 (d, J=6.4 Hz, 6H). LC-MS (m/z) 383.2 (MH⁺); $t_R$=2.76 (Method C).

Example 9: 5-[(4-methoxyphenyl)methyl]-6-(oxetan-3-ylmethyl)-1-tetrahydropyran-4-yl-pyrazolo[3,4-d]pyrimidin-4-one

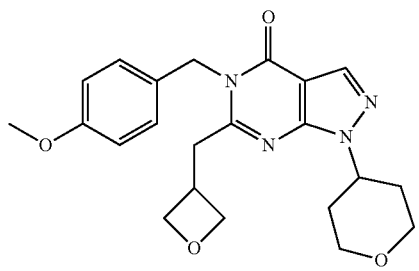 [SMILES: COc1ccc(Cn2c(CC3COC3)nc3c(cnn3C3CCOCC3)c2=O)cc1]

Prepared from 6-(oxetan-3-ylmethyl)-1-(tetrahydro-2H-pyran-4-yl)-1,5-dihydro-4H-pyrazolo[3,4-d]pyrimidin-4-one and 1-(chloromethyl)-4-methoxybenzene.

¹H NMR (CDCl₃ 400 MHz): δ 8.07 (s, 1H), 7.08 (d, J=8.8 Hz, 2H), 6.85 (d, J=8.4 Hz, 2H), 5.36 (bs, 2H), 4.84-4.78 (m, 1H), 4.17-4.13 (m, 2H), 3.78 (s, 3H), 3.64-3.58 (m, 2H), 3.18-3.13 (m, 1H), 2.47-2.38 (m, 2H), 1.98-1.94 (m, 2H), 1.24-1.22 (d, J=6.4 Hz, 6H). LC-MS (m/z) 411.2 (MH⁺); t$_R$=2.07 (Method B).

Example 10: 5-[(3-fluorophenyl)methyl]-6-methyl-1-tetrahydropyran-4-yl-pyrazolo[4,3-c]pyridin-4-one

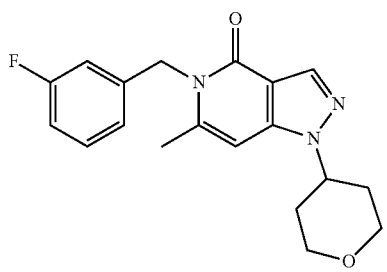 [SMILES: Cc1cc2c(cnn2C2CCOCC2)c(=O)n1Cc1cccc(F)c1]

Prepared from 6-methyl-1-(tetrahydro-2H-pyran-4-yl)-1,5-dihydro-4H-pyrazolo[4,3-c]pyridin-4-one and 1-(bromomethyl)-3-fluorobenzene.

¹H NMR (CDCl₃ 400 MHz): δ 8.16 (s, 1H), 7.25 (m, 1H), 6.93 (d, J=7.6 Hz, 2H), 6.81 (d, J=9.6 Hz, 1H), 6.27 (s, 1H), 5.36 (br.s, 2H), 4.44-4.38 (m, 1H), 4.16 (d, J=9.2 Hz, 2H), 3.57 (t, J=11.6 Hz, 2H), 2.41-2.37 (m, 5H), 1.94 (d, J=12.8 Hz, 2H). LC-MS (m/z) 342.2 (MH⁺); t$_R$=2.35 (Method C).

Example 11: 5-[(2-fluorophenyl)methyl]-6-methyl-1-tetrahydropyran-4-yl-pyrazolo[4,3-c]pyridin-4-one

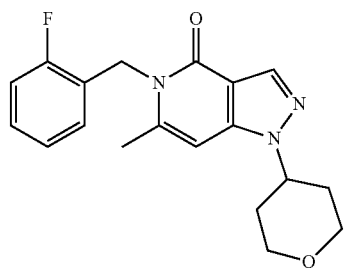 [SMILES: Cc1cc2c(cnn2C2CCOCC2)c(=O)n1Cc1ccccc1F]

Prepared from 6-methyl-1-(tetrahydro-2H-pyran-4-yl)-1,5-dihydro-4H-pyrazolo[4,3-c]pyridin-4-one and 1-(bromomethyl)-2-fluorobenzene.

¹H NMR (CDCl₃ 400 MHz): δ 8.16 (s, 1H), 7.23-7.21 (m, 1H), 7.08-6.94 (m, 3H), 6.27 (s, 1H), 5.42 (s, 2H), 4.41 (t, J=11.6 Hz, 1H), 4.16 (d, J=9.6 Hz, 2H), 3.57 (t, J=12.0 Hz, 2H), 2.41-2.34 (m, 5H), 1.94 (d, J=12.0 Hz, 2H). LC-MS (m/z) 342.2 (MH⁺); t$_R$=2.36 (Method C).

Example 12: 5-[(4-chlorophenyl)methyl]-6-methyl-1-tetrahydropyran-4-yl-pyrazolo[4,3-c]pyridin-4-one

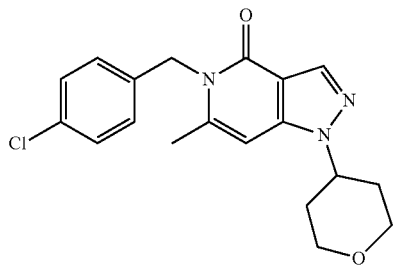 [SMILES: Cc1cc2c(cnn2C2CCOCC2)c(=O)n1Cc1ccc(Cl)cc1]

Prepared from 6-methyl-1-(tetrahydro-2H-pyran-4-yl)-1,5-dihydro-4H-pyrazolo[4,3-c]pyridin-4-one and 1-(bromomethyl)-4-chlorobenzene.

¹H NMR (CDCl₃ 400 MHz): δ 8.16 (s, 1H), 7.27 (d, J=7.2 Hz, 2H), 7.09 (d, J=8.4 Hz, 2H), 6.26 (s, 1H), 5.33 (br. s, 2H), 4.44-4.37 (m, 1H), 4.16 (dd, J=11.6 Hz, J=3.6 Hz, 2H), 3.57 (t, J=12.0 Hz, 2H), 2.42-2.34 (m, 5H), 1.94 (dd, J=12.8 Hz, J=2.4 Hz, 2H). LC-MS (m/z) 358.1 (MH⁺); t$_R$=2.52 (Method C).

Example 13: 5-benzyl-6-methyl-1-tetrahydropyran-4-yl-pyrazolo[4,3-c]pyridin-4-one

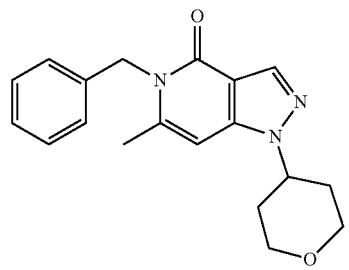 [SMILES: Cc1cc2c(cnn2C2CCOCC2)c(=O)n1Cc1ccccc1]

Prepared from 6-methyl-1-(tetrahydro-2H-pyran-4-yl)-1,5-dihydro-4H-pyrazolo[4,3-c]pyridin-4-one and (bromomethyl)benzene.

¹H NMR (CDCl₃ 400 MHz): δ 8.18 (s, 1H), 7.30-7.26 (m, 3H), 7.16 (m, 2H), 6.26 (s, 1H), 5.40 (br. s, 2H), 4.42 (m, 1H), 4.17 (d, J=10.8 Hz, 2H), 3.58 (t, J=10.8 Hz, 2H), 2.36 (m, 5H), 1.96 (d, J=13.2 Hz, 2H). LC-MS (m/z) 324.2 (MH⁺); t$_R$=2.11 (Method C).

Example 14: 5-[(3-chlorophenyl)methyl]-6-methyl-1-tetrahydropyran-4-yl-pyrazolo[4,3-c]pyridin-4-one

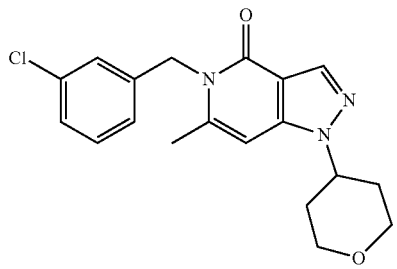 [SMILES: Cc1cc2c(cnn2C2CCOCC2)c(=O)n1Cc1cccc(Cl)c1]

Prepared from 6-methyl-1-(tetrahydro-2H-pyran-4-yl)-1,5-dihydro-4H-pyrazolo[4,3-c]pyridin-4-one and 1-(bromomethyl)-3-chlorobenzene.

$^1$H NMR (CDCl3 400 MHz): δ 8.20-8.18 (m, 1H), 7.29-7.24 (m, 2H), 7.15-7.13 (m, 1H), 7.05 (s, 1H), 6.31-6.28 (m, 1H), 5.36 (br. s, 2H), 4.45-4.40 (m, 1H), 4.18 (d, J=8.0 Hz, 2H), 3.61-3.56 (m, 2H), 2.40-2.35 (m, 5H), 1.97 (m, 2H). LC-MS (m/z) 358.2 (MH$^+$); $t_R$=2.29 (Method C).

Example 15: 5-[(4-fluorophenyl)methyl]-6-methyl-1-tetrahydropyran-4-yl-pyrazolo[4,3-c]pyridin-4-one

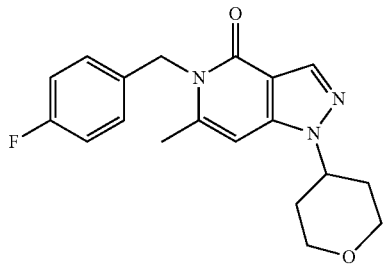 [SMILES: Cc1cc2c(cnn2C2CCOCC2)c(=O)n1Cc1ccc(F)cc1]

Prepared from 6-methyl-1-(tetrahydro-2H-pyran-4-yl)-1,5-dihydro-4H-pyrazolo[4,3-c]pyridin-4-one and 1-(bromomethyl)-4-fluorobenzene.

$^1$H NMR (CDCl$_3$ 400 MHz): δ 8.17 (s, 1H), 7.16-7.13 (m, 2H), 6.99 (t, J=8.4 Hz, 2H), 6.27 (s, 1H), 5.35 (br. s, 2H), 4.44-4.39 (m, 1H), 4.17 (d, J=9.2 Hz, 2H), 3.58 (t, J=12.0 Hz, 2H), 2.42-2.36 (m, 5H), 1.95 (d, J=12.4 Hz, 2H). LC-MS (m/z) 342.2 (MH$^+$); $t_R$=2.16 (Method C).

Example 16: 6-methyl-5-(p-tolylmethyl)-1-tetrahydropyran-4-yl-pyrazolo[4,3-c]pyridin-4-one

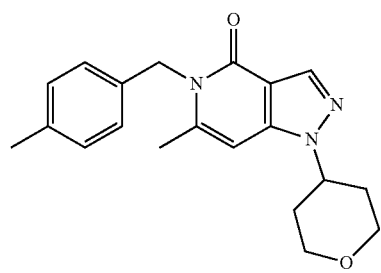 [SMILES: Cc1ccc(Cn2c(C)cc3c(cnn3C3CCOCC3)c2=O)cc1]

Prepared from 6-methyl-1-(tetrahydro-2H-pyran-4-yl)-1,5-dihydro-4H-pyrazolo[4,3-c]pyridin-4-one and 1-(bromomethyl)-4-methylbenzene.

$^1$H NMR (CDCl$_3$ 400 MHz): δ 8.18 (s, 1H), 7.12-7.04 (m, 4H), 6.24 (s, 1H), 5.35 (br. s, 2H), 4.41 (m, 1H), 4.17 (d, J=9.6 Hz, 2H), 3.58 (t, J=12.0 Hz, 2H), 2.42-2.31 (m, 8H), 1.95 (d, J=12.8 Hz, 2H). LC-MS (m/z) 338.2 (MH$^+$); $t_R$=2.04 (Method B).

Example 17: 5-(1,3-benzodioxol-5-ylmethyl)-6-methyl-1-tetrahydropyran-4-yl-pyrazolo[4,3-c]pyridin-4-one

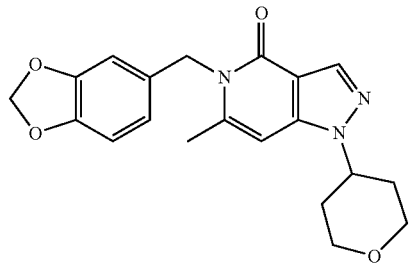 [SMILES: Cc1cc2c(cnn2C2CCOCC2)c(=O)n1Cc1ccc2c(c1)OCO2]

Prepared from 6-methyl-1-(tetrahydro-2H-pyran-4-yl)-1,5-dihydro-4H-pyrazolo[4,3-c]pyridin-4-one and 5-(bromomethyl)benzo[d][1,3]dioxole.

$^1$H NMR (CDCl$_3$ 400 MHz): δ 8.16 (s, 1H), 6.73 (d, J=8.0 Hz, 1H), 6.66-6.62 (m, 2H), 6.25 (s, 1H), 5.92 (s, 2H), 5.28 (s, 2H), 4.44-4.38 (m, 1H), 4.18-4.15 (m, 2H), 3.60-3.55 (m, 2H), 2.43-2.32 (m, 5H), 1.96-1.93 (m, 2H). LC-MS (m/z) 368.2 (MH$^+$); $t_R$=2.26 (Method C).

Example 18: 5-[(6-methoxy-3-pyridyl)methyl]-6-methyl-1-tetrahydropyran-4-yl-pyrazolo[4,3-c]pyridin-4-one

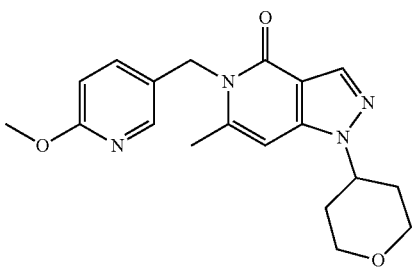 [SMILES: COc1ccc(Cn2c(C)cc3c(cnn3C3CCOCC3)c2=O)cn1]

Prepared from 6-methyl-1-(tetrahydro-2H-pyran-4-yl)-1,5-dihydro-4H-pyrazolo[4,3-c]pyridin-4-one and 5-(chloromethyl)-2-methoxypyridine.

$^1$H NMR (CDCl$_3$ 400 MHz): δ 8.15 (s, 1H), 8.01 (s, 1H), 7.51-7.49 (m, 1H), 6.68 (d, J=8.8 Hz, 1H), 6.25 (s, 1H), 5.29 (s, 2H), 4.42-4.36 (m, 1H), 4.17-4.14 (m, 2H), 3.89 (s, 3H), 3.59-3.53 (m, 2H), 2.40-2.30 (m, 5H), 1.94-1.91 (m, 2H). LC-MS (m/z) 355.2 (MH$^+$); $t_R$=1.84 (Method B).

Example 19: 5-(4-methoxybenzyl)-6-methyl-1-(tetrahydro-2H-pyran-4-yl)-1,5-dihydro-4H-pyrazolo[4,3-c]pyridin-4-one

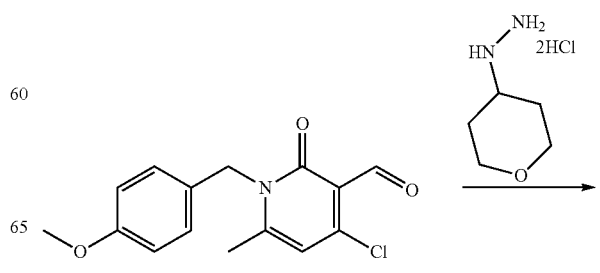

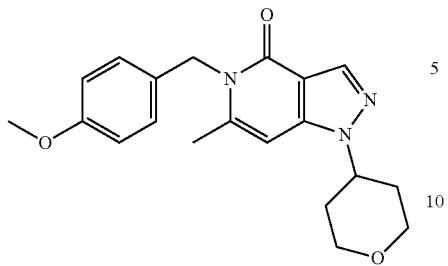

Triethylamine (198 mg, 0.27 mL, 2.0 mmol) was added to 4-chloro-1-(4-methoxybenzyl)-6-methyl-2-oxo-1,2-dihydropyridine-3-carbaldehyde (100 mg, 0.34 mmol) and (tetrahydro-2H-pyran-4-yl)hydrazine dihydrochloride (65 mg, 0.34 mmol) in ethanol (2.5 mL). The reaction mixture was heated by microwave irradiation (130° C. for 30 minutes then 150° C. for 20 minutes). The reaction mixture was concentrated in vacuo. The crude material was purified via flash chromatography on silica gel (using a gradient of heptane and ethyl acetate) to give 5-(4-methoxybenzyl)-6-methyl-1-(tetrahydro-2H-pyran-4-yl)-1,5-dihydro-4H-pyrazolo[4,3-c]pyridin-4-one (9 mg, 7% yield).

$^1$H NMR (DMSO d$_6$ 600 MHz) δ 8.07 (s, 1H), 7.05 (d, J=8.6 Hz, 2H), 6.88 (d, J=8.7 Hz, 2H), 6.73 (s, 1H), 5.25 (bs, 2H), 4.71-4.64 (m, 1H), 3.99 (dd, J=11.3, 4.1 Hz, 2H), 3.71 (s, 3H), 3.50 (dd, J=11.8, 10.7 Hz, 2H), 2.33 (s, 3H), 2.08 (qd, J=12.6, 4.8 Hz, 2H), 1.85 (dd, J=12.5, 2.4 Hz, 2H). LC-MS (m/z) 354.1 (MH$^+$); t$_R$=0.59 (Method D).

The following compounds were prepared in a similar manner:

Example 20: 5-(4-methoxybenzyl)-6-methyl-1-propyl-1,5-dihydro-4H-pyrazolo[4,3-c]pyridin-4-one

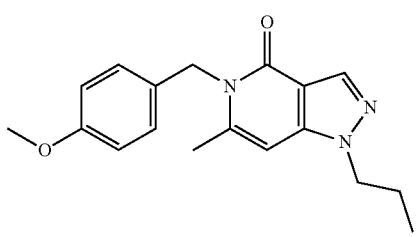 [SMILES: CCCn1ncc2c(=O)n(Cc3ccc(OC)cc3)c(C)cc21]

Prepared from 4-chloro-1-(4-methoxybenzyl)-6-methyl-2-oxo-1,2-dihydropyridine-3-carbaldehyde and propylhydrazine.

$^1$H NMR (DMSO d$_6$ 600 MHz) δ 8.04 (s, 1H), 7.05 (d, J=8.7 Hz, 2H), 6.88 (d, J=8.7 Hz, 2H), 6.65 (s, 1H), 5.24 (bs, 2H), 4.19 (t, J=6.9 Hz, 2H), 3.71 (s, 3H), 2.32 (s, 3H), 1.80 (h, J=7.2 Hz, 2H), 0.82 (t, J=7.4 Hz, 3H). LC-MS (m/z) 312 (MH$^+$); t$_R$=0.65 (Method E).

Example 21: 1-isopropyl-5-[(4-methoxyphenyl)methyl]-6-methyl-pyrazolo[4,3-c]pyridin-4-one

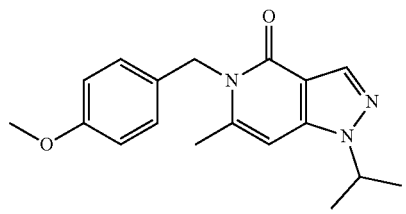 [SMILES: COc1ccc(Cn2c(C)cc3c(cnn3C(C)C)c2=O)cc1]

Prepared from 4-chloro-1-(4-methoxybenzyl)-6-methyl-2-oxo-1,2-dihydropyridine-3-carbaldehyde and isopropylhydrazine hydrochloride.

$^1$H NMR (CDCl$_3$ 400 MHz): δ 8.16 (s, 1H), 7.10 (d, J=8.4 Hz, 2H), 6.82 (d, J=8.4 Hz, 2H), 6.20 (s, 1H), 5.30 (br.s, 2H), 4.61-4.54 (m, 1H), 3.76 (s, 3H), 2.35 (s, 3H), 1.54 (d, J=6.8 Hz, 6H). LC-MS (m/z) 312.1 (MH$^+$); t$_R$=2.52 (Method C).

Example 22: 5-[(4-methoxyphenyl)methyl]-6-methyl-1-tetrahydrofuran-3-yl-pyrazolo[4,3-c]pyridin-4-one

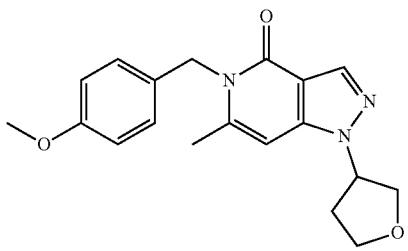 [SMILES: COc1ccc(Cn2c(C)cc3c(cnn3C3CCOC3)c2=O)cc1]

Prepared from 4-chloro-1-(4-methoxybenzyl)-6-methyl-2-oxo-1,2-dihydropyridine-3-carbaldehyde and (tetrahydrofuran-3-yl)hydrazine hydrochloride.

$^1$H NMR (CDCl$_3$ 400 MHz): δ 8.23-8.15 (m, 1H), 7.09-7.06 (m, 2H), 6.81 (d, J=8.4 Hz, 2H), 6.37-6.26 (m, 1H), 5.29-5.26 (m, 2H), 5.09-5.02 (m, 1H), 4.25-4.12 (m, 3H), 3.97-3.95 (m, 1H), 3.75 (s, 3H), 2.56-2.30 (m, 5H). LC-MS (m/z) 340.2 (MH$^+$); t$_R$=2.24 (Method C).

Example 23: 1-cyclopropyl-5-[(4-methoxyphenyl)methyl]-6-methyl-pyrazolo[4,3-c]pyridin-4-one

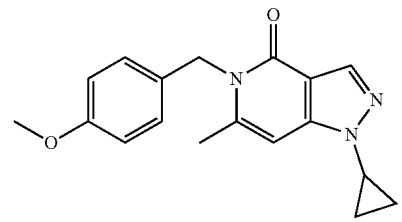 [SMILES: COc1ccc(Cn2c(C)cc3c(cnn3C3CC3)c2=O)cc1]

Prepared from 4-chloro-1-(4-methoxybenzyl)-6-methyl-2-oxo-1,2-dihydropyridine-3-carbaldehyde and cyclopropylhydrazine hydrochloride.

$^1$H NMR (CDCl$_3$ 400 MHz): δ 8.09 (s, 1H), 7.09 (d, J=8.4 Hz, 2H), 6.82 (d, J=8.4 Hz, 2H), 6.36 (s, 1H), 5.31 (s, 2H), 3.77 (s, 3H), 3.44-3.49 (m, 1H), 2.37 (s, 3H), 1.09-1.20 (m, 4H). LC-MS (m/z) 310.2 (MH+); $t_R$=2.16 (Method B).

Example 24: 1-ethyl-5-[(4-methoxyphenyl)methyl]-6-methyl-pyrazolo[4,3-c]pyridin-4-one

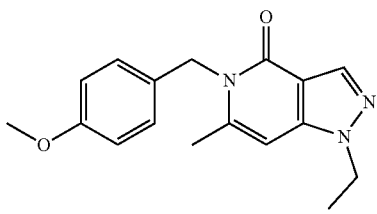 [SMILES: CCn1ncc2c(=O)n(Cc3ccc(OC)cc3)c(C)cc21]

Prepared from 4-chloro-1-(4-methoxybenzyl)-6-methyl-2-oxo-1,2-dihydropyridine-3-carbaldehyde and ethylhydrazine oxalate.

$^1$H NMR (CDCl$_3$ 400 MHz): δ 8.15 (s, 1H), 7.10 (d, J=8.4 Hz, 2H), 6.83 (d, J=8.4 Hz, 2H), 6.19 (s, 1H), 5.32 (br. s, 2H), 4.24 (q, J=7.6 Hz, 2H), 3.77 (s, 3H), 2.37 (s, 3H), 1.49 (t, J=7.6 Hz, 3H). LC-MS (m/z) 298.2 (MH+); $t_R$=2.33 (Method C).

Example 25: 5-[(4-methoxyphenyl)methyl]-6-methyl-1-tetrahydropyran-3-yl-pyrazolo[4,3-c]pyridin-4-one

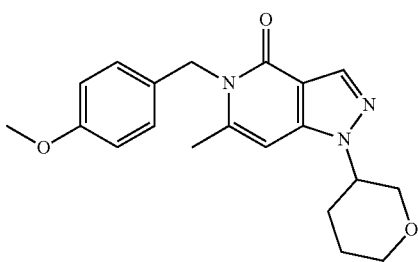 [SMILES: COc1ccc(Cn2c(C)cc3c(cnn3C3CCCOC3)c2=O)cc1]

Prepared from 4-chloro-1-(4-methoxybenzyl)-6-methyl-2-oxo-1,2-dihydropyridine-3-carbaldehyde and (tetrahydro-2H-pyran-3-yl)hydrazine hydrochloride.

$^1$H NMR (CDCl$_3$ 400 MHz): δ 8.15 (s, 1H), 7.09 (d, J=8.4 Hz, 2H), 6.81 (d, J=8.4 Hz, 2H), 6.22 (s, 1H), 5.30 (br. s, 2H), 4.31-4.29 (m, 1H), 4.03-3.98 (m, 2H), 3.76 (s, 4H), 3.52-3.46 (m, 1H), 2.36-2.28 (m, 4H), 2.19-2.16 (m, 1H), 1.86 (m, 2H). LC-MS (m/z) 354.2 (MH+); $t_R$=2.18 (Method B).

Example 26: 5-[(4-methoxyphenyl)methyl]-6-methyl-1-[(trans)-2-methyltetrahydrofuran-3-yl]pyrazolo[4,3-c]pyridin-4-one

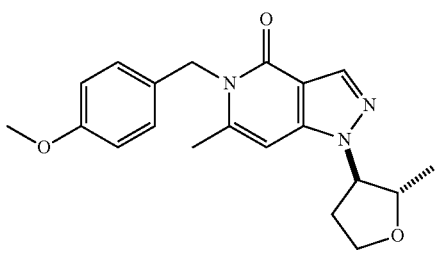

Prepared from 4-chloro-1-(4-methoxybenzyl)-6-methyl-2-oxo-1,2-dihydropyridine-3-carbaldehyde and trans-(2-methyltetrahydrofuran-3-yl)hydrazine hydrochloride $^1$H NMR (CDCl$_3$ 400 MHz): δ 8.20 (s, 1H), 7.11 (d, J=8.4 Hz, 2H), 6.84 (d, J=8.4 Hz, 2H), 6.21 (s, 1H), 5.33 (br. s, 2H), 4.44-4.40 (m, 1H), 4.24-4.14 (m, 3H), 3.78 (s, 3H), 2.57-2.47 (m, 2H), 2.38 (s, 3H), 1.32 (d, J=5.6 Hz, 3H). LC-MS (m/z) 354.2 (MH+); $t_R$=2.37 (Method C).

Example 27: 5-[(4-methoxyphenyl)methyl]-6-methyl-1-[(cis)-2-methyltetrahydrofuran-3-yl]pyrazolo[4,3-c]pyridin-4-one

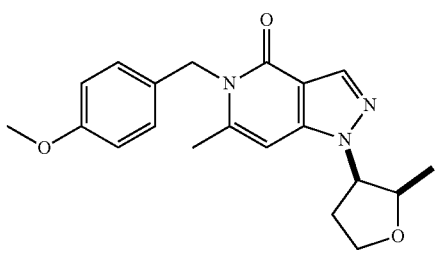

Prepared from 4-chloro-1-(4-methoxybenzyl)-6-methyl-2-oxo-1,2-dihydropyridine-3-carbaldehyde and cis-(2-methyltetrahydrofuran-3-yl) hydrazine hydrochloride $^1$H NMR (CDCl$_3$ 400 MHz): δ 8.18 (s, 1H), 7.10 (d, J=8.4 Hz, 2H), 6.82 (d, J=8.4 Hz, 2H), 6.21 (s, 1H), 5.37-5.23 (m, 2H), 4.90 (bs, 1H), 4.41-4.39 (m, 1H), 4.09-4.06 (m, 1H), 3.88-3.82 (m, 1H), 3.76 (s, 3H), 2.64-2.56 (m, 2H), 2.36 (s, 3H), 0.84 (d, J=6.0 Hz, 3H). LC-MS (m/z) 354.2 (MH+); $t_R$=2.28 (Method C).

Example 28: 5-(4-methoxybenzyl)-6-methyl-1-(oxetan-3-yl)-1,5-dihydro-4H-pyrazolo[4,3-c]pyridin-4-one

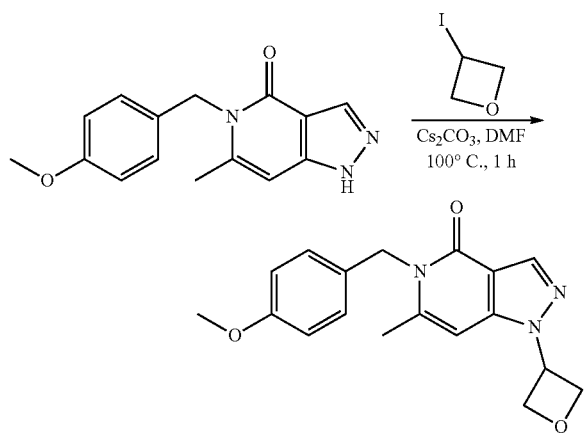

A mixture of 5-(4-methoxybenzyl)-6-methyl-1,5-dihydro-4H-pyrazolo[4,3-c]pyridin-4-one (30 mg, 0.111 mmol), 3-iodooxetane (41 mg, 0.223 μmol) and Cs$_2$CO$_3$ (109 mg, 334 mmol) in DMF (3 mL) was stirred at 100° C. for 1 hour under microwave irradiation. The mixture was filtered and purified by basic preparative HPLC followed by purification by SFC to give 5-(4-methoxybenzyl)-6-methyl-1-(oxetan-3-yl)-1,5-dihydro-4H-pyrazolo[4,3-c]pyridin-4-one (35 mg, 36% yield).

$^1$H NMR (CDCl$_3$ 400 MHz): δ 8.23 (s, 1H), 7.08 (d, J=8.4 Hz, 2H), 6.81 (d, J=8.4 Hz, 2H), 6.31 (s, 1H), 5.59-5.52 (m, 1H), 5.31 (br.s, 2H), 5.21 (t, J=6.4 Hz, 2H), 5.08 (t, J=7.6 Hz, 2H), 3.76 (s, 3H), 2.37 (s, 3H). LC-MS: $t_R$=2.080 min (Method C), m/z=326.1 [M+H]$^+$.

SFC Method:

Instrument: SFC-13; Column: Chiralpak AS (250 mm×30 mm, 5 um); Mobile phase: Base-ETOH=40/60 at 40 mL/min; Column Temp: 38° C.; Nozzle Pressure: 100 Bar; Nozzle Temp: 60° C.; Evaporator Temp: 20° C.; Trimmer Temp: 25° C.

Example 29: 5-(4-methoxybenzyl)-6-methyl-1-(4-methyltetrahydro-2H-pyran-4-yl)-1,5-dihydro-4H-pyrazolo[4,3-c]pyridin-4-one

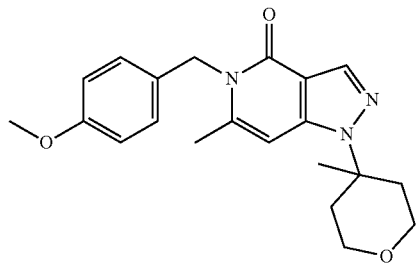 [SMILES: COc1ccc(Cn2c(C)cc3c(cnn3C3(C)CCOCC3)c2=O)cc1]

Prepared as example 19 from 4-chloro-1-(4-methoxybenzyl)-6-methyl-2-oxo-1,2-dihydropyridine-3-carbaldehyde and (4-methyltetrahydro-2H-pyran-4-yl)hydrazine hydrochloride.

$^1$H NMR (CDCl$_3$ 400 MHz): δ 8.16 (s, 1H), 7.14 (d, J=8.4 Hz, 2H), 6.84 (d, J=8.8 Hz, 2H), 6.35 (s, 1H), 5.32 (s, 2H), 3.78-3.71 (m, 7H), 2.67-2.63 (m, 2H), 2.37 (s, 3H), 2.05-2.03 (m, 2H), 1.62 (s, 3H). LC-MS (m/z) 368.2 (MH$^+$); $t_R$=2.23 (Method C).

In Vitro Testing

PDE1 Inhibition Assay

PDE1A, PDE1B and PDE1C assays were performed as follows: the assays was performed in 60 μL samples containing a fixed amount of the PDE1 enzyme (sufficient to convert 20-25% of the cyclic nucleotide substrate), a buffer (50 mM HEPES pH 7.6; 10 mM MgCl$_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 hr at room temperature before being terminated through mixing with 20 μL (0.2 mg) yttrium silicate SPA beads (PerkinElmer). The beads were allowed to settle for 1 hr in the dark before the plates were counted in a Wallac 1450 Microbeta counter. The measured signals were converted to activity relative to an uninhibited control (100%) and IC$_{50}$ values were calculated using XlFit (model 205, IDBS).

PDE9 Inhibition Assay

A PDE9 assay may for example, be performed as follows: The assay is performed in 60 μL samples containing a fixed amount of the relevant PDE enzyme (sufficient to convert 20-25% of the cyclic nucleotide substrate), a buffer (50 mM HEPES pH 7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 μL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

In the context of the present invention the assay was performed in 60 uL assay buffer (50 mM HEPES pH 7.6; 10 mM MgCl$_2$; 0.02% Tween20) containing enough PDE9 to convert 20-25% of 10 nM $^3$H-cAMP and varying amounts of inhibitors. Following 1 hr incubation the reactions were terminated by addition of 15 uL 8 mg/mL yttrium silicate SPA beads (Amersham). The beads were allowed to settle for one hr in the dark before the plates were counted in a Wallac 1450 Microbeta counter.

The invention claimed is:

1. A compound of formula (I):

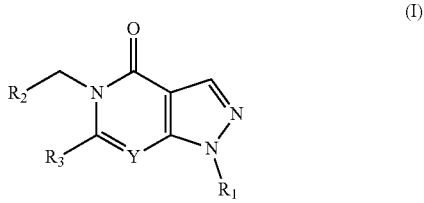

wherein:

Y is N or CH;

R$_1$ is selected from the group consisting of linear or branched C$_2$-C$_8$ alkyl, saturated monocyclic C$_3$-C$_8$ cycloalkyl, oxetanyl, tetrahydrofuranyl and tetrahydropyranyl; all of which can be substituted one or more times with one or more substituents selected from the group consisting of methyl, fluorine, hydroxy, cyano and methoxy;

R$_2$ is:
(a) selected from the group consisting of linear or branched C$_1$-C$_8$ alkyl, phenyl, benzo[1,3]dioxole and saturated monocyclic C$_3$-C$_8$ cycloalkyl; or
(b) phenyl substituted one or more times with one or more substituents selected from the group consisting of halogen, C$_1$-C$_3$ alkyl and methoxy; or
(c) pyridyl substituted with a substituent selected from the group consisting of halogen, C$_1$-C$_3$ alkyl, C$_1$-C$_3$ alkoxy, C$_1$-C$_3$ fluoroalkoxy, C$_3$-C$_4$ cycloalkoxy and C$_4$-C$_5$ methylcycloalkoxy; or
(d) selected from the group consisting of 5-membered heteroaryls substituted with C$_1$-C$_3$ alkyl;

and

R$_3$ is selected from the group consisting of linear or branched C$_1$-C$_3$ alkyl and saturated monocyclic C$_3$-C$_8$ cycloalkyl; which can each be optionally substituted with a substituent selected from halogen, C$_1$-C$_3$ alkoxy, phenyl, dialkylamine and oxetane;

or a tautomer or pharmaceutically acceptable salt thereof.

2. The compound or tautomer or pharmaceutically acceptable salt thereof of claim 1, wherein Y is N.

3. The compound or tautomer or pharmaceutically acceptable salt thereof of claim 1, wherein Y is CH.

4. The compound or tautomer or pharmaceutically acceptable salt thereof of claim 1, wherein R$_1$ is a linear or branched C$_2$-C$_8$ alkyl or a saturated monocyclic C$_3$-C$_8$ cycloalkyl.

5. The compound or tautomer or pharmaceutically acceptable salt thereof of claim 1, wherein $R_1$ is oxetanyl, tetrahydrofuranyl or tetrathydropyranyl.

6. The compound or tautomer or pharmaceutically acceptable salt thereof of claim 1, wherein $R_2$ is:
   (a) phenyl optionally substituted one or more times with one or more substituents selected from the group consisting of methyl, methoxy, fluorine and chlorine; or
   (b) pyridyl substituted with a substituent selected from the group consisting of methyl, methoxy, fluorine and chlorine.

7. The compound or tautomer or pharmaceutically acceptable salt thereof of claim 1, wherein $R_2$ is a saturated monocyclic $C_3$-$C_8$ cycloalkyl.

8. The compound or tautomer or pharmaceutically acceptable salt thereof of claim 1, wherein $R_3$ is $C_{1-3}$ alkyl.

9. The compound or tautomer or pharmaceutically acceptable salt thereof of claim 1, wherein $R_3$ is methyl substituted with a phenyl.

10. The compound or tautomer or pharmaceutically acceptable salt thereof of claim 1, wherein $R_3$ is methyl substituted with a methoxy or oxetane.

11. The compound or tautomer or pharmaceutically acceptable salt thereof of claim 1, wherein:
   $R_2$ is:
      (a) selected from the group consisting of phenyl, benzo[1,3]dioxole, and saturated monocyclic $C_3$-$C_8$ cycloalkyl; or
      (b) phenyl substituted one or more times with one or more substituents selected from the group consisting of halogen, $C_1$-$C_3$ alkyl and $C_1$-$C_3$ alkoxy; or
      (c) pyridyl substituted with a substituent selected from the group consisting of halogen, $C_1$-$C_3$ alkyl and $C_1$-$C_3$ alkoxy, $C_1$-$C_3$ fluoroalkoxy, $C_3$-$C_4$ cycloalkoxy and $C_4$-$C_5$ methylcycloalkoxy;
   and
   $R_3$ is $C_1$-$C_3$ alkyl which can each be optionally substituted with a substituent selected from the group consisting of halogen, $C_1$-$C_3$ alkoxy, phenyl and oxetane.

12. The compound or tautomer or pharmaceutically acceptable salt thereof of claim 1, wherein the compound is selected from the group consisting of:
   6-benzyl-5-(cyclohexylmethyl)-1-tetrahydropyran-4-yl-pyrazolo[3,4-d]pyrimidin-4-one;
   5-(4-methoxybenzyl)-6-methyl-1-(tetrahydro-2H-pyran-4-yl)-1H-pyrazolo[3,4-d]pyrimidin-4(5H)-one;
   5-(cyclohexylmethyl)-6-methyl-1-tetrahydropyran-4-yl-pyrazolo[3,4-d]pyrimidin-4-one;
   5-[(4-methoxyphenyl)methyl]-6-methyl-1-propyl-pyrazolo[3,4-d]pyrimidin-4-one;
   5-(cyclohexylmethyl)-6-methyl-1-propyl-pyrazolo[3,4-d]pyrimidin-4-one;
   6-ethyl-5-[(4-methoxyphenyl)methyl]-1-tetrahydropyran-4-yl-pyrazolo[3,4-d]pyrimidin-4-one;
   6-(methoxymethyl)-5-[(4-methoxyphenyl)methyl]-1-tetrahydropyran-4-yl-pyrazolo[3,4-d]pyrimidin-4-one;
   6-isopropyl-5-[(4-methoxyphenyl)methyl]-1-tetrahydropyran-4-yl-pyrazolo[3,4-d]pyrimidin-4-one;
   5-[(4-methoxyphenyl)methyl]-6-(oxetan-3-ylmethyl)-1-tetrahydropyran-4-yl-pyrazolo[3,4-d]pyrimidin-4-one;
   5-[(3-fluorophenyl)methyl]-6-methyl-1-tetrahydropyran-4-yl-pyrazolo[4,3-c]pyridin-4-one;
   5-[(2-fluorophenyl)methyl]-6-methyl-1-tetrahydropyran-4-yl-pyrazolo[4,3-c]pyridin-4-one;
   5-[(4-chlorophenyl)methyl]-6-methyl-1-tetrahydropyran-4-yl-pyrazolo[4,3-c]pyridin-4-one;
   5-benzyl-6-methyl-1-tetrahydropyran-4-yl-pyrazolo[4,3-c]pyridin-4-one;
   5-[(3-chlorophenyl)methyl]-6-methyl-1-tetrahydropyran-4-yl-pyrazolo[4,3-c]pyridin-4-one;
   5-[(4-fluorophenyl)methyl]-6-methyl-1-tetrahydropyran-4-yl-pyrazolo[4,3-c]pyridin-4-one;
   6-methyl-5-(p-tolylmethyl)-1-tetrahydropyran-4-yl-pyrazolo[4,3-c]pyridin-4-one;
   5-(1,3-benzodioxol-5-ylmethyl)-6-methyl-1-tetrahydropyran-4-yl-pyrazolo[4,3-c]pyridin-4-one;
   5-[(6-methoxy-3-pyridyl)methyl]-6-methyl-1-tetrahydropyran-4-yl-pyrazolo[4,3-c]pyridin-4-one;
   5-(4-methoxybenzyl)-6-methyl-1-(tetrahydro-2H-pyran-4-yl)-1,5-dihydro-4H-pyrazolo[4,3-c]pyridin-4-one;
   5-(4-methoxybenzyl)-6-methyl-1-propyl-1,5-dihydro-4H-pyrazolo[4,3-c]pyridin-4-one;
   1-isopropyl-5-[(4-methoxyphenyl)methyl]-6-methyl-pyrazolo[4,3-c]pyridin-4-one;
   5-[(4-methoxyphenyl)methyl]-6-methyl-1-tetrahydrofuran-3-yl-pyrazolo[4,3-c]pyridin-4-one;
   1-cyclopropyl-5-[(4-methoxyphenyl)methyl]-6-methyl-pyrazolo[4,3-c]pyridin-4-one;
   1-ethyl-5-[(4-methoxyphenyl)methyl]-6-methyl-pyrazolo[4,3-c]pyridin-4-one;
   5-[(4-methoxyphenyl)methyl]-6-methyl-1-tetrahydropyran-3-yl-pyrazolo[4,3-c]pyridin-4-one;
   5-[(4-methoxyphenyl)methyl]-6-methyl-1-[(2S,3R)-2-methyltetrahydrofuran-3-yl]pyrazolo[4,3-c]pyridin-4-one;
   5-[(4-methoxyphenyl)methyl]-6-methyl-1-[(2R,3R)-2-methyltetrahydrofuran-3-yl]pyrazolo[4,3-c]pyridin-4-one;
   5-[(4-methoxyphenyl)methyl]-6-methyl-1-(oxetan-3-yl)pyrazolo[4,3-c]pyridin-4-one; and
   5-(4-methoxybenzyl)-6-methyl-1-(4-methyltetrahydro-2H-pyran-4-yl)-1,5-dihydro-4H-pyrazolo[4,3-c]pyridin-4-one.

13. A pharmaceutical composition comprising a therapeutically effective amount of the compound or tautomer or pharmaceutically acceptable salt thereof of claim 1 and one or more pharmaceutically acceptable carriers, diluents and excipients.

14. A pharmaceutical composition comprising a therapeutically effective amount of the compound or tautomer or pharmaceutically acceptable salt thereof of claim 11 and one or more pharmaceutically acceptable carriers, diluents and excipients.

15. A pharmaceutical composition comprising a therapeutically effective amount of the compound or tautomer or pharmaceutically acceptable salt thereof of claim 12 and one or more pharmaceutically acceptable carriers, diluents and excipients.

* * * * *